(12) United States Patent
Hafenstine et al.

(10) Patent No.: US 11,649,410 B2
(45) Date of Patent: *May 16, 2023

(54) BIODERIVED FUELS AND METHODS OF MAKING THE SAME

(71) Applicant: Alliance for Sustainable Energy, LLC, Golden, CO (US)

(72) Inventors: Glenn Richard Hafenstine, Wheat Ridge, CO (US); Derek Richard Vardon, Lakewood, CO (US); Xiangchen Huo, Golden, CO (US); Nabila Asem Huq, Boulder, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/379,477

(22) Filed: Jul. 19, 2021

(65) Prior Publication Data
US 2021/0340452 A1    Nov. 4, 2021

Related U.S. Application Data

(63) Continuation of application No. 15/930,205, filed on May 12, 2020, now Pat. No. 11,098,257.
(Continued)

(51) Int. Cl.
| | |
|---|---|
| *C10L 1/02* | (2006.01) |
| *C07C 41/09* | (2006.01) |
| *B01J 27/195* | (2006.01) |
| *B01J 23/44* | (2006.01) |
| *B01J 35/10* | (2006.01) |

(Continued)

(52) U.S. Cl.
CPC .............. *C10L 1/026* (2013.01); *C07C 41/09* (2013.01); *C10L 1/02* (2013.01); *C10L 1/023* (2013.01); *B01J 23/44* (2013.01); *B01J 27/1802* (2013.01); *B01J 27/195* (2013.01); *B01J 35/023* (2013.01); *B01J 35/026* (2013.01); *B01J 35/1014* (2013.01); *B01J 35/1019* (2013.01); *B01J 35/1038* (2013.01); *B01J 35/1042* (2013.01); *C10L 2200/0423* (2013.01);
(Continued)

(58) Field of Classification Search
CPC .......... C07C 41/09; C10L 1/023; C10L 1/026; C10L 2270/023
See application file for complete search history.

(56) References Cited

U.S. PATENT DOCUMENTS

| | | |
|---|---|---|
| 11,098,257 B2 | 8/2021 | Hafenstine et al. |
| 2014/0051872 A1 | 2/2014 | Blank et al. |
| 2015/0166918 A1 | 6/2015 | Ford |

OTHER PUBLICATIONS

Fioroni, G. et al., Screening of potential biomass-derived streams as fuel blendstocks for mixing controlled compression ignition combustion, Apr. 2, 2019, SAE Technical Paper 2-019=01-0570, 22 pages (with appendix) (Year: 2019).*

(Continued)

*Primary Examiner* — Yate' K Cutliff
(74) *Attorney, Agent, or Firm* — Michael A. McIntyre

(57) ABSTRACT

The present disclosure relates to a composition that includes a first oxide having a phosphate, a ratio of Brønsted acid sites to Lewis acid sites between 0.05 and 1.00, and a total acidity between 50 μmol/g and 300 μmol/g, where the phosphate is at least one of a functional group covalently bonded to the first oxide and/or an anion ionically bonded to the first oxide.

12 Claims, 27 Drawing Sheets

Related U.S. Application Data

(60) Provisional application No. 62/847,700, filed on May 14, 2019.

(51) Int. Cl.
*B01J 35/02* (2006.01)
*B01J 27/18* (2006.01)

(52) U.S. Cl.
CPC . *C10L 2200/0446* (2013.01); *C10L 2270/023* (2013.01); *C10L 2270/026* (2013.01)

(56) References Cited

OTHER PUBLICATIONS

Balakrishnan et al., "Etherification and reductive etherification of 5-(hydroxymethyl)furfural: 5-(alkoxymethyl) furfurals and 2,5-bis(alkoxymethyl)furans as potential bio-diesel candidates", Green Chemistry, 2012, vol. 14, No. 6, pp. 1626-1634.
Bethmont et al., "An Alternative Catalytic Method to the Williamson's Synthesis of Ethers", Tetrahedron Letters, 1995, vol. 36, pp. 4235-4236.
Bethmont et al., "Ether synthesis from alcohol and aldehyde in the presence of hydrogen and palladium deposited on charcoal", Journal of Molecular Catalysis A: Chemical, 2000, vol. 152, pp. 133-140.
Bringué et al., "Kinetics of 1-hexanol etherification on Amberlyst 70", Chemistry—Chemical Engineering Journal, 2014, vol. 246, pp. 71-78.
Carniti et al., "Intrinsic and Effective Acidity Study of Niobic Acid and Niobium Phosphate by a Multitechnique Approach", Chesmistry of Materials, 2005, vol. 17, No. 24, pp. 6128-6136.
Carniti et al., "Niobic acid and niobium phosphate as highly acidic viable catalysts in aqueous medium: Fructose dehydration reaction", Catalysis Today, Dec. 2006, vol. 118, Nos. 3-4, pp. 373-378.
Carniti et al., Silica—niobia oxides as viable acid catalysts in water: Effective vs. intrinsic acidity. Catalysis Today, Jul. 2010,152, Nos. 1-4, pp. 42-47.
Carniti et al., "Cooperative action of Brønsted and Lewis acid sites of niobiumphosphate catalysts for cellobiose conversion in water", Applied Catalysis B: Environmental, 2016, vol. 193, pp. 93-102.
Davies et al., Dehydrative Etherification Reactions of Glycerol with Alcohols Catalyzed by Recyclable Nanoporous Aluminosilicates: Telescoped Routes to Glyceryl Ethers, ACS Sustainable Chemistry & Engineering, Nov. 2015, vol. 4, No. 3, pp. 835-843.
Eagan et al., "Catalytic synthesis of distillate-range ethers and olefins from ethanol through Guerbet coupling and etherification". Green Chemistry, 2019, vol. 21, pp. 3300-3318.
Eagan et al., "Correction: Catalytic synthesis of distillate-range ethers and olefins from ethanol through Guerbet coupling and etherification", Green Chemistry, 2019, vol. 21, pp. 5128-5129.
Fairly, "Introduction: Next generation biofuels", Nature, Jun. 2011, vol. 474, No. 7352, pp. S2-S5.
Fioroni et al., "Screening of Potential Biomass-Derived Streams as Fuel Blendstocks for Mixing Controlled Compression Ignition Combustion", SAE International:, Apr. 2019, Detroit, pp. 1-17.
Fioroni et al., "Screening of Potential Biomass-Derived Streams as Fuel Blendstocks for Mixing Controlled Compression Ignition Combustion", SAE International:, Apr. 2019, SAE Technical Paper 2019-010570, pp. 1-22.
Fujii et al., "A Convenient Catalytic Method for the Synthesis of Ethers from Alcohols and Carbonyl Compounds", Bulletin of the Chemical Society of Japan, 2005, 78, No. 3, pp. 456-463.
Foo et al., "Role of Lewis and Brønsted Acid Sites in the Dehydration of Glycerol over Niobia", ACS Catalysis, Aug. 2014, vol. 4, No. 9, pp. 3180-3192.
Gaertner et al., "Catalytic coupling of carboxylic acids by ketonization as a processing step in biomass conversion", Journal of Catalysis, 2009, vol. 266, No. 1, pp. 71-78.
Garcia-Ortiz et al., "Transforming Methyl Levulinate into Biosurfactants and Biolubricants by Chemoselective Reductive Etherification with Fatty Alcohols", ChemSusChem, 2020, vol. 13, No. 4, pp. 707-714.
Gooßen et al., "Catalytic Reductive Etherification of Ketones with Alcohols at Ambient Hydrogen Pressure: A Practical, Waste-Minimized Synthesis of Dialkyl Ethers", Synlett, 2006, vol. 20, pp. 3489-3491.
Jadhav et al., "Production of Biomass-Based Automotive Lubricants by Reductive Etherification", ChemSusChem, 2017, vol. 10, pp. 2527-2533.
Ji et al., "Investigation on performance of a spark-ignition engine fueled with dimethyl ether and gasoline mixtures under idle and stoichiometric conditions", Energy, May 2017, vol. 126, pp. 335-342.
Kiss et al., "Solid Acid Catalysts for Biodiesel Production—Towards Sustainable Energy", Advanced Synthesis & Catalysis, Jan. 2006, vol. 348, pp. 75-81.
Lee et al., "Direct Hydrogenation of Biomass-Derived Butyric Acid to n-Butanol over a Ruthenium-Tin Bimetallic Catalyst", ChemSusChem Communications, Aug. 2014, vol. 7, No. 11, pp. 2998-3001.
Li et al., "A cobalt catalyst for reductive etherification of 5-hydroxymethyl-furfural to 2,5-bis(methoxymethyl)furan under mild conditions", Green Chemistry, 2018, vol. 20, pp. 1095-1105.
Long et al., "Doping Pd/SiO2 with Na+ : changing the reductive etherification of C═O to furan ring hydrogenation of furfural in ethanol", RSC Advances, 2019, vol. 9, No. 44, pp. 25345-25350.
Luijkx et al., "Ether Formation in the Hydrogenolysis of Hydroxymethylfurfural Over Palladium Catalysts in Alcoholic Solution", Heterocycles, 2009, vol. 77, No. 2, pp. 1037-1044.
Magar et al., "Solid-Acid Catalyzed Etherification of Glycerol to Potential Fuel Additives", Energy Fuels, 2017, vol. 31, pp. 12272-12277.
Nakajima et al., "Nb2O5—nH2O as a Heterogeneous Catalyst with Water-Tolerant Lewis Acid Sites", Journal of the American Chemical Society, Mar. 2011, vol. 133, No. 12, pp. 4224-4227.
Nagashima et al., "Ketonization of carboxylic acids over CeO2-based composite oxides", Journal of Molecular Catalysis A: Chemical, 2005, vol. 227, No. 1, pp. 231-239.
Okuhara, "Water-Tolerant Solid Acid Catalysts", Chemical Reviews, Sep. 2002, vol. 102, No. 10, pp. 3641-3666.
Pham et al., "Etherification of aldehydes, alcohols and their mixtures on Pd/SiO2 catalysts", Applied Catalysis A: General, 2010, vol. 379, pp. 135-140.
Pizzi et al., "High-Throughput Screening of Heterogeneous Catalysts for the Conversion of Furfural to Bio-Based Fuel Components", Catalysts, 2015, vol. 5, No. 4, pp. 2244-2257.
Rocha et al., "Comparative performance of niobium phosphates in liquid phase anisole benzylation with benzyl alcohol", Catalysis Communications, 2008, vol. 9, pp. 1959-1965.
Rorrer et al., "Effect of Alcohol Structure on the Kinetics of Etherification and Dehydration over Tungstated Zirconia", ChemSusChem, 2018, vol. 11, pp. 3104-3111.
Scaldaferri et al., "Production of jet fuel and green diesel range biohydrocarbons by hydroprocessing of soybean oil over niobium phosphate catalyst", Fuel, 2019, vol. 245, pp. 458-466.
Topgül, "The effects of MTBE blends on engine performance and exhaust emissions in a spark ignition engine", Fuel Processing Technology, 2015, vol. 138, pp. 483-489.
Tulchinsky et al., "One-Pot Synthesis of Alkyl 4-Alkoxypentanoates by Esterification and Reductive Etherification of Levulinic Acid in Alcoholic Solutions", ACS Sustainable Chemistry & Engineering, 2016, vol. 4, pp. 4089-4093.
Tsuchida et al., "Copper-and-Borinic Acid-catalyzed Propargylic Etherification of Propargylic Carbonates with Benzyl Alcohols", Chemistry Letters, 2018, vol. 47, pp. 671-673.
Wang et al., "Facile synthesis of furfuryl ethyl ether in high yield via the reductive etherification of furfural in ethanol over Pd/C under mild conditions", Green Chemistry, 2018, vol. 20, pp. 2110-2117.
Wei et al., "A Carbon-Free Li2TiO3/Li2MTi3O8(M═Zn1/3Co2/3)Nanocomposite as High-Rate and Long-Life Anode forLithium-Ion Batteries", Energy Technology, 2019, vol. 7, pp. 1801071-1800960.

(56) References Cited

OTHER PUBLICATIONS

West et al., "Production of alkanes from biomass derived carbohydrates on bi-functional catalysts employing niobium-based supports", Catalysis Communications, 2009, vol. 10, pp. 1743-1746.
Xiong et al., "Hydrothermally stable heterogeneous catalysts for conversion of biorenewables", Green Chemistry, 2014, vol. 16, pp. 4627-4643.

\* cited by examiner

BIODERIVED FUELS AND METHODS OF MAKING THE SAME

CROSS-REFERENCE TO RELATED APPLICATIONS

This application is a continuation application of U.S. patent application Ser. No. 15/930,205 filed on May 12, 2020, which claims priority from U.S. Provisional Patent Application No. 62/847,700 filed May 14, 2019, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Reductive etherification is a promising catalytic chemistry for coupling biomass derived alcohols and ketones to produce branched ethers that can be used as high cetane, low sooting blendstocks for diesel fuel applications. Previous catalyst materials examined for reductive etherification have typically been limited to binary physical mixtures of metal hydrogenation and acidic acetalization catalysts with limited thermal stability and industrial applicability. Thus, there remains a need for improved catalysts and methods for producing fuels and chemicals from bioderived alcohols and ketones.

SUMMARY

An aspect of the present disclosure is a composition that includes a first oxide having a phosphate, a ratio of Brønsted acid sites to Lewis acid sites between 0.05 and 1.00, and a total acidity between 50 µmol/g and 300 µmol/g, where the phosphate is at least one of a functional group covalently bonded to the first oxide and/or an anion ionically bonded to the first oxide. In some embodiments of the present disclosure, the phosphated first oxide may include at least one of $Nb_2O_5$—$PO_4$, $TiO_2$—$PO_4$, $ZrO_2$—$PO_4$, $NbOPO_4$, $ZrO_2$—$PO_4$, $WO_3$—$PO_4$, $Ti(HPO_4)_2$, and/or $Zr(HPO_4)_2$.

In some embodiments of the present disclosure, the composition may further include a surface area between about 40 $m^2/g$ and about 500 $m^2/g$. In some embodiments of the present disclosure, the composition may further include a pore volume between 0.05 $cm^3/g$ and about 1.0 $cm^3/g$. In some embodiments of the present disclosure, the composition may further include a particle positioned on a surface of the first oxide, where the particle includes a transition metal. In some embodiments of the present disclosure, the transition metal may include at least one of palladium, platinum, ruthenium, rhodium, iridium, molybdenum, nickel, cobalt, and/or copper. In some embodiments of the present disclosure, the particle may have a characteristic length between about 0.1 nm and about 10 µm. In some embodiments of the present disclosure, the particle may have a characteristic length between about 10 µm and about 3 mm. In some embodiments of the present disclosure, a concentration of the particle may be between about 0.1 wt % and about 15 wt %.

In some embodiments of the present disclosure, the composition may further include a second oxide that is different than the first oxide, where the second oxide forms a core having a surface, and the first oxide forms a shell covering substantially all of the surface. In some embodiments of the present disclosure, the second oxide may include at least one of $Nb_2O_5$, $ZrO_2$, $Al_2O_3$, and/or $TiO_2$.

An aspect of the present disclosure is a composition that includes a first mixture that includes an ether defined by

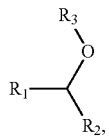

where each of $R_1$ and $R_2$ include a hydrogen atom or an aliphatic group, and $R_3$ includes an aliphatic group. In some embodiments of the present disclosure, each of $R_1$, $R_2$, and $R_3$ may have between 1 and 30 carbon atoms, inclusively. In some embodiments of the present disclosure, each aliphatic group may include at least one of an alkyl group, an alkenyl group, or an alkynyl group. In some embodiments of the present disclosure, the ether may include at least one of 4-butoxyheptane, 1-isopropoxybutane, 4-hexoxyheptane, 6-ethoxyundecane, 4-octoxyheptane, 4-ethoxyheptane, dibutyl ether, and/or ethyl tetrahydrofurfuryl ether.

In some embodiments of the present disclosure, the first mixture may further include at least one of an alcohol and/or a ketone. In some embodiments of the present disclosure, the ether may be present in the first mixture at a concentration between about 1 wt % and about 100 wt %. In some embodiments of the present disclosure, the composition may further include a second mixture that includes at least one of a diesel fuel and/or a gasoline fuel. In some embodiments of the present disclosure, the first mixture may be present at a concentration between about 10 vol % and about 100 vol %. In some embodiments of the present disclosure, the composition may further include a CN value greater than 40. In some embodiments of the present disclosure, the composition may further include an LHV value greater than 25 MJ/kg. In some embodiments of the present disclosure, the composition may further include an LHV value greater than 36 MJ/kg. In some embodiments of the present disclosure, the composition may further include a water solubility less than 2 g/L.

An aspect of the present disclosure is a method that includes reacting in the presence of a solid catalyst, diatomic hydrogen gas with a mixture comprising an alcohol and a ketone, where the reacting results in the forming of an ether.

BRIEF DESCRIPTION OF THE DRAWINGS

Some embodiments are illustrated in referenced figures of the drawings. It is intended that the embodiments and figures disclosed herein are to be considered illustrative rather than limiting.

Figure 1:
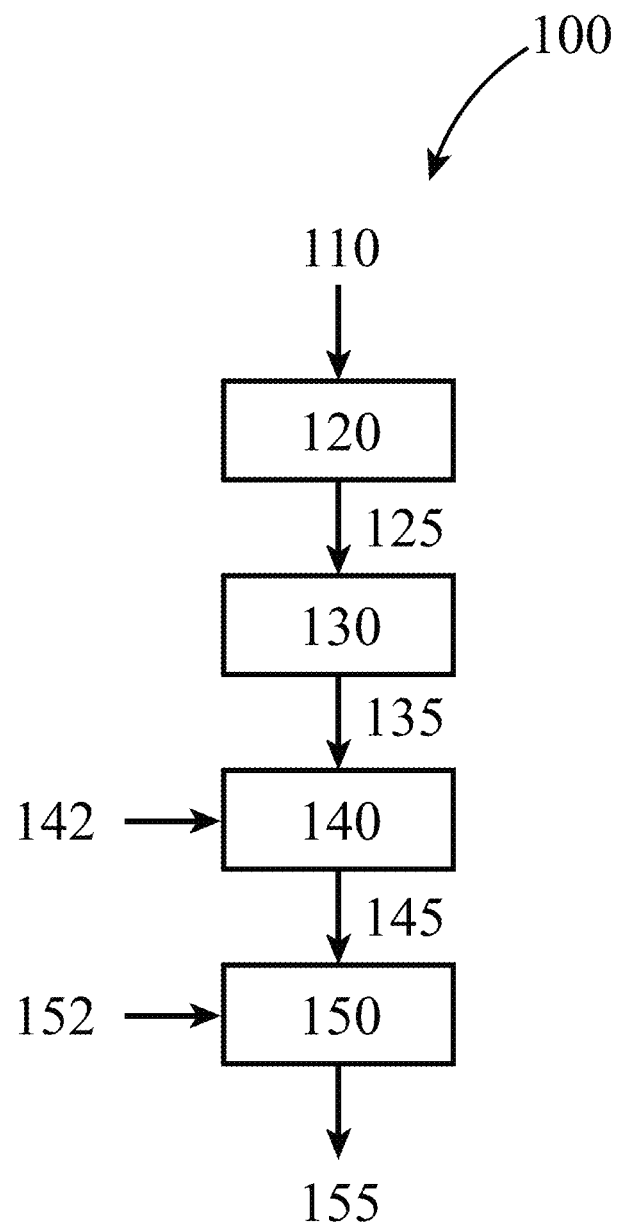
FIG. 1 illustrates a method for using a catalyst to produce bioderived fuels including ethers, according to some embodiments of the present disclosure.

| REFERENCE NUMBERS | |
|---|---|
| 100 | method |
| 110 | biomass |
| 120 | degrading |
| 125 | degradation product |
| 130 | separating |
| 135 | separation product |
| 140 | reacting |
| 142 | hydrogen (H2) |
| 145 | ether |
| 150 | blending |
| 152 | blend component |
| 155 | fuel |
| 200 | catalyst |
| 210 | core |
| 220 | shell |
| 230 | particle |
| 240 | functional group |

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult-to-define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to reacting an alcohol with a ketone and hydrogen ($H_2$) to form an ether and water, as shown below in Reaction (1). In some embodiments of the present disclosure, Reaction (1) may be catalyzed using at least one of a homogenous and/or a heterogeneous catalyst (not shown). The resultant ether, as described herein, may be utilized by itself and/or blended with other molecules to form a liquid fuel.

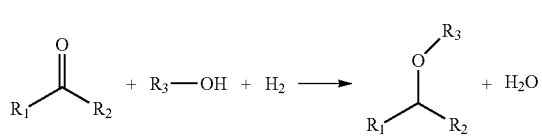

(1)

$R_1$, $R_2$, and $R_3$ may be any suitable functional group. As used herein, the term "functional group" refers to any relatively small group of atoms covalently attached to an atom, in the case $R_1$ and $R_2$ of Reaction (1), to a carbon atom, and in the case of $R_3$, to an oxygen atom. For example, a functional group may be an aliphatic group and/or hydrogen. As used herein, an "aliphatic group" denotes a hydrocarbon moiety that may be a straight-chain (i.e. unbranched), branched, or cyclic (including fused, bridging, and/or a spiro-fused polycyclic compounds) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. A functional group may be an oxygenate, where the term "oxygenate" refers to any aliphatic group containing the element oxygen. In some embodiments of the present disclosure, a functional group may contain other elements, including at least one of nitrogen, sulfur, phosphorus, and/or a halogen.

Reaction (2) illustrates a more specific example of Reaction (1), according to some embodiments of the present disclosure. In this reaction, n-butanol is reacted with 4-heptanone and hydrogen to form 4-butoxyheptane and water. The resultant 4-butoxyheptane, as described herein, may be utilized by itself and/or blended with other molecules to form a liquid fuel.

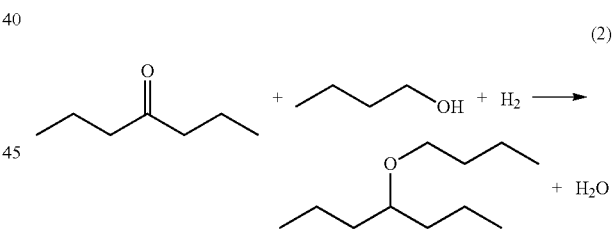

(2)

In some embodiments of the present disclosure, an ether (e.g. 4-butoxyheptane) may be used for, among other things, as a fuel where the fuel may be bioderived. For example, at least one of the ethers and/or fuels described herein may stem from biomass (e.g. lignin, cellulose, and/or hemicellulose), where the biomass has been deconstructed and/or depolymerized to form the starting reactants, at least one of an alcohol, a ketone, and/or hydrogen ($H_2$). FIG. 1 illustrates a method 100 that converts biomass 110 to a fuel 155 by, among other things, reacting an alcohol, a ketone, and hydrogen 142 to form an ether 145, where the fuel 155 contains at least the ether 145.

In some embodiments of the present disclosure, a method 100 for making a fuel 155 may begin with the degrading 120 of biomass 110. Biomass 100 may include cellulose, hemicellulose, lignin, proteins, lipids, fatty acids, and/or other components. Biomass 100 may include residential waste, agricultural waste, and/or any other suitable material. Further examples of biomass 100 include bagasse, wheat straw, corn stover, grasses, wood mixed food wastes, palm oil mill effluent, corn mill stillage, sludge, animal manure, food processing rejects, and algae. The degrading 120 may be performed by chemical, thermal, and/or biological degradation and/or depolymerization of at least one of the various components of the biomass 100 being utilized as the feedstock. The specific method of degrading 120 will depend on the specific composition and makeup of the biomass 100. Examples of unit operations suitable for the degrading 120 of biomass 100 include fermentation, pyrolysis, gasification, steam explosion, acid/base liquid treating, etc. The result of the degrading 120 is the production of degradation products 135, including carboxylic acids such as butyric acid, alcohols such as n-butanol, syngas containing hydrogen and carbon monoxide, and/or various lignin degradation products such as guaiacol. In some embodiments of the present disclosure, the degradation products 135 may be processed further by the separating 130 of at least some of the individual components contained in the degradation products 135 to produce at least one relatively pure separation product 135 (e.g. alcohols, ketones, and/or $H_2$). Examples of separation products 135 include alcohols (e.g. ethanol, n-butanol), esters (e.g. ethyl acetate, butyl butyrate), ketones (e.g. methyl ethyl ketone, 4-heptanone), and hydrogen. The separating 130 of the various components making up the degradation products 125 may be accomplished by any suitable unit operation and will be determined by the specific component mix. Examples of suitable separation methods include at least one of distillation, crystallization, adsorption, extraction, dewatering, flocculation, filtration and/or gravimetric methods.

Referring again to the method 100 illustrated in FIG. 1, the separation products 135, including alcohols, ketones, and hydrogen ($H_2$), may be directed to a reacting 140 step. In some embodiments of the present disclosure, a separation product 135 that includes at least one alcohol and at least one ketone may be directed as a mixture to the reacting 140 step where the alcohol and the ketone may be combined with hydrogen 142 resulting in a reaction (see Reactions (1) and (2) above) to form an ether 145. In some embodiments of the present disclosure, the reaction of the alcohol and the ketone with hydrogen may by catalyzed. As described herein, a catalyst used for reacting an alcohol, a ketone, and hydrogen to form an ether 145 may be a homogeneous and/or a heterogeneous catalyst. In some cases, a catalyst for reacting an alcohol, a ketone, and $H_2$ to form an ether may be a solid catalyst.

In some embodiments of the present disclosure, the reacting 140 may be performed by heating the mixture to an average temperature between about 50° C. and about 300° C., or between about 100° C. and about 200° C. In some embodiments of the present disclosure, the reacting 140 may be performed at a total pressure between about 0 psig and about 2000 psig, or between about 0 psig and about 1000 psig. Further, the reacting 140 may be performed where all of the components taking part in the reaction are in the liquid phase, except the $H_2$, which may be present in the gas phase and/or partially dissolved in the liquid phase. In some embodiments of the present disclosure, the reacting 140 may be performed in at least one of a batch reactor and/or a continuous reactor. In some embodiments of the present disclosure, the reacting 140 may be performed in a batch reactor, where the materials (reactants and/or products) have a residence time in the batch reactor between about 1 hour and about 10 hours, or between about 1 hour and about 5 hours. In some embodiments of the present disclosure, the reacting 140 may be performed in a flow reactor, where the materials have a weight hourly space velocity (WHSV) in the flow reactor between about 0.1 h$^{-1}$ and about 10 h$^{-1}$, or between about 1 h$^{-1}$ and about 2 h$^{-1}$.

In some embodiments of the present disclosure, the alcohol reacted with the ketone in the reacting 140 may include at least one of a primary alcohol, a secondary alcohol, and/or a tertiary alcohol having between one and 20 carbon atoms. For example, the alcohol reacted with the ketone may be a primary alcohol such as ethanol, propanol, and/or butanol. In some embodiments of the present disclosure, the ketone reacted with the alcohol in the reacting 140 may have the structure

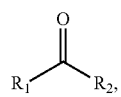

where $R_1$ includes at least one of a hydrogen atom or a first aliphatic group, and $R_2$ comprises at least one of a hydrogen atom or a second aliphatic group. The first aliphatic group and the second aliphatic may be the same or different. In some embodiments of the present disclosure, an aliphatic group may include at least one of alkyl group, an alkenyl group, or alkynyl group, an alcohol group, and/or an ester group. In some embodiments of the present disclosure, a ketone may include at least one ketone having between 3 and 20 carbon atoms, for example 4-heptanone, and may be a terminal ketone and/or a central ketone. In some embodiments of the present disclosure, the ether 145 resulting from the reacting 140 of hydrogen 142, an alcohol, and a ketone, in the presence of a catalyst, may produce an ether 145 having between 4 and 30 carbon atoms (as determined by any possible combination of reacting one or more alcohols with one or more ketones), for example 4-butoxyheptane. Finally, the method 100 may proceed to a blending 150, where the ether(s) 145 may be combined with at least one blend component 152 to produce a fuel 155. In some embodiments of the present disclosure, a blend component may include at least one of a petrochemical diesel, a green diesel, a biodiesel, and/or a gasoline.

Figure 2:
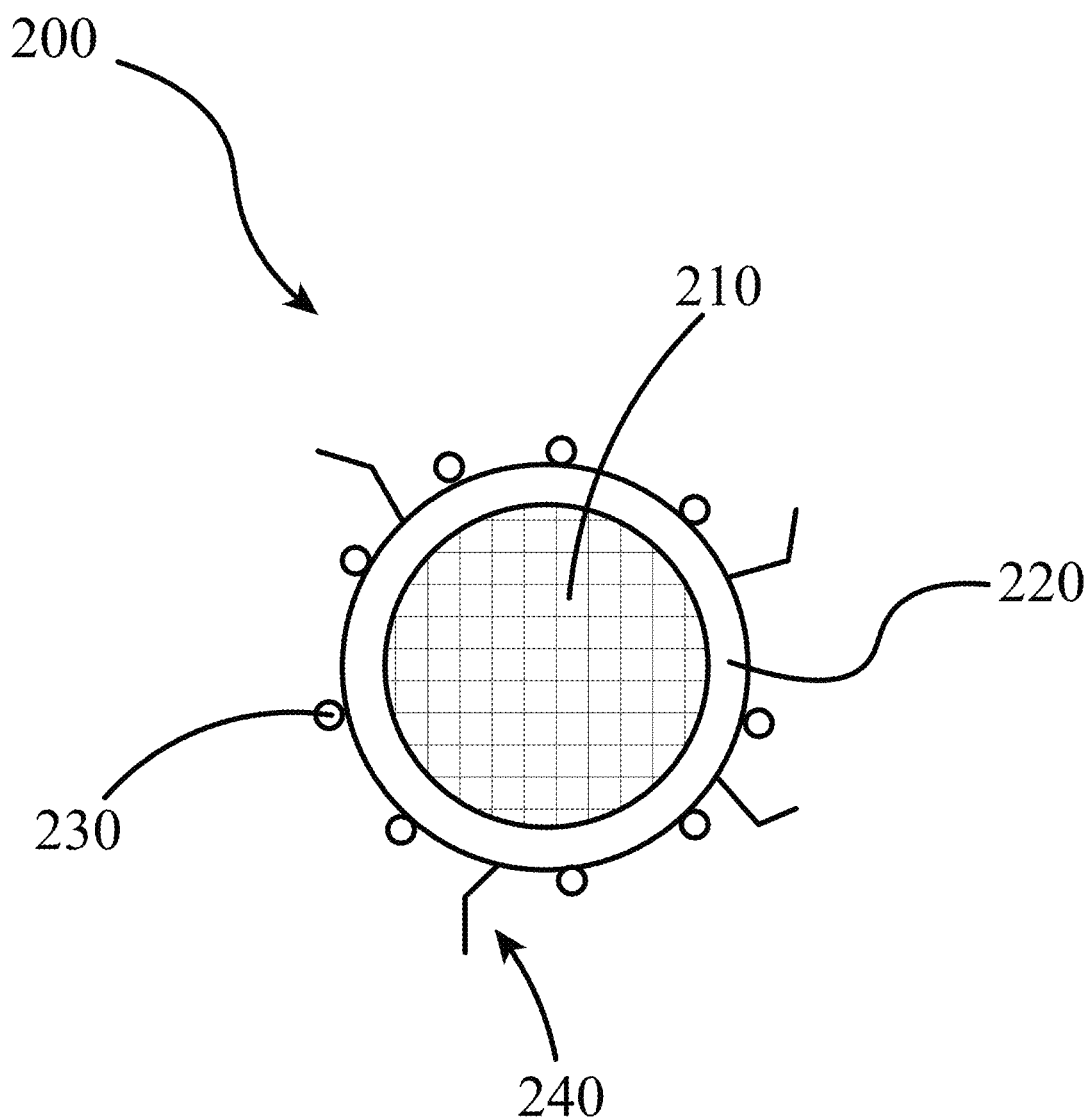
FIG. 2 illustrates a catalyst for converting bioderived reactants to fuels including ethers, according to some embodiments of the present disclosure.

FIG. 2 illustrates a catalyst 200, which may be utilized for Reactions (1) and/or (2), according to some embodiments of the present disclosure. This exemplary catalyst 200 includes a core 210 having a first outer surface, a shell 220 having a second outer surface, where the shell 220 substantially covers the first outer surface, a particle 230 positioned on the second outer surface, and a functional group 240 covalently bonded to the shell 220. In some embodiments of the present disclosure, the core 210 may include at least one of a first oxide, a first phosphate, and/or a carbonaceous material such as an activated carbon. The first oxide may include at least one of a transition metal, aluminum, silicon, and/or magnesium. In some embodiments of the present disclosure, the first oxide may include at least one of niobium, zirconium, aluminum, titanium, tantalum, hafnium, scandium, yttrium, lanthanum, tungsten, and/or molybdenum. For example, the core 210 may include a first oxide that includes at least one of $Nb_2O_5$, $ZrO_2$, $Al_2O_3$, and/or $TiO_2$. In some embodiments of the present disclosure, the first phosphate may include at least one of niobium, zirconium, aluminum, titanium, tantalum, hafnium, scandium, yttrium, lanthanum, tungsten, and/or molybdenum. For example, the core 210 may include a first phosphate that includes at least one of $Nb_2P_4O_{15}$, $LaPO_4$ and/or $Zr(HPO_4)_2$. In some embodiments of the present disclosure, the core may have a characteristic length (e.g. diameter) between about 10 microns and about 3 mm, or between about 10 microns and about 500 microns (e.g. for powders). In some embodiments of the present disclosure, a functional group may be covalently or ionically bonded to the catalyst. In some embodiments of the present disclosure, a functional group may be bonded to at least one of an external and/or an internal surface of the catalyst. In some embodiments of the present disclosure, a functional group may include at least one of a phosphate, a sulfate, and/or a tungstate.

In some embodiments of the present disclosure, the shell 220 of a catalyst 200 may further include a second oxide. The second oxide of the shell 220 may include at least one of a transition metal, aluminum, silicon, and/or magnesium. In some embodiments of the present disclosure, the second oxide may include at least one of niobium, zirconium, aluminum, titanium, tantalum, hafnium, scandium, yttrium, lanthanum, tungsten, and/or molybdenum. For example, the shell 220 may include a second oxide that includes at least one of $Nb_2O_5$, $ZrO_2$, $Al_2O_3$, and/or $TiO_2$. In some embodiments of the present disclosure, the shell 220 of the catalyst 200 may have a thickness between about 1 nanometer and about 10 micron, or between about 1 nanometer and about 100 nanometers.

In some embodiments of the present disclosure, a particle 230 positioned on the surface of the shell 220 of a catalyst 200 may include a transition metal, for example, at least one of palladium, platinum, ruthenium, rhodium, iridium, molybdenum, nickel, cobalt, and/or copper. A particle 230 may have a characteristic length between about 0.1 nanometers and 10 micron, or between about 0.1 nanometers and about 50 nanometers. In some embodiments of the present disclosure, the particles 230 may be present on the catalyst 200 at a concentration between about 0.1 wt % and about 15 wt %, or between about 1 wt % and about 5 wt %. Referring again to FIG. 2, in some embodiments of the present disclosure, a functional group 240 bonded to the catalyst 200, e.g. bonded to at least a portion of the shell 220, may include at least one oxygen, phosphorous, carbon, sulfur, or nitrogen. For example, a catalyst 200 may include a functional group 240 that includes at least one of $-SO_3H$, $-PO_4H_2$, $-COOH$, $-SH$, $-OH$, $-NH_2$, and/or a heteropolyacid. In some embodiments of the present disclosure, a functional group 240 may be present at a concentration between about 0.1 wt % and about 15 wt % when measured in the elemental form of S, P, C, or N, or between about 3 wt % and about 6 wt %. In some embodiments of the present disclosure, a catalyst 200 may have a surface area between about 10 $m^2/g$ and about 1500 $m^2/g$ as measured by nitrogen physisorption, a porosity between about 0.1 mL/g and about 0.9 mL/g, and/or an acidity between about 10 umol/g and about 5000 umol/g, or between about 10 umol/g and about 3000 umol/g, as measured by ammonia temperature programmed desorption.

As described herein, in some embodiments of the present disclosure, a catalyst 200 like that illustrated in FIG. 2 may be used to catalyze reactions between alcohols and ketones to produce ethers 145, which may by themselves, or when blended with at least one blend component 152, be used as fuels 155 having unique and desirable properties. For example, a fuel may be produced using the catalysts and methods described herein, that includes 4-butoxyheptane. In some embodiments of the present disclosure, a fuel may further include at least one of n-butanol and/or 4-heptanone. In some embodiments of the present disclosure, the fuel may be produced by blending the fuel containing 4-butoxyheptane with at least one of a petrochemical diesel, a green diesel, a biodiesel, and/or a gasoline.

In some embodiments of the present disclosure, such a fuel may have desirable physical and/or performance properties, including, among other things, at least one of a freeze temperature between less than or equal to about −80° C. and less than or equal to about 10° C., a cloud point temperature between less than or equal to about −80° C. and less than or equal to about 10° C., a cetane (CN) between about 10 and about 120, a sooting tendency quantified by yield sooting index (YSI) between about 10 and about 210, with YSI based on the linear dimensionless scale of YSI-heptane=36 and YSI-toluene=170.9 and/or a flash point between about 52° C. and about 100° C. (See FIG. 7 and related text for more details.)

Figure 3:
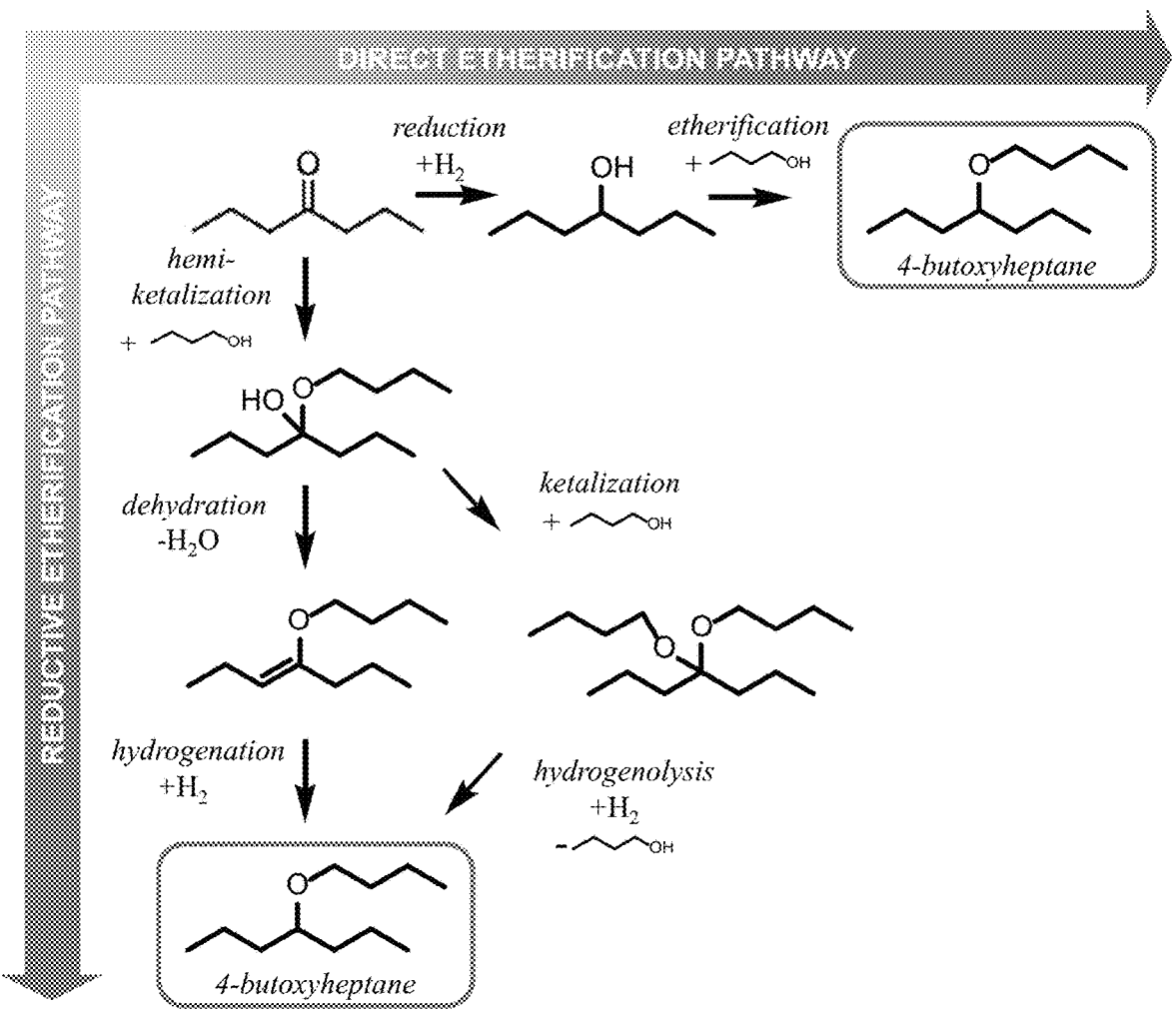
FIG. 3 illustrates a reaction scheme for producing 4-butoxyheptane from n-butanol and 4-heptanone, according to some embodiments of the present disclosure.

The methods and catalysts described above, and the resultant ether products and fuels have been tested, as described herein. In order to both demonstrate a successful conversion process towards a novel target $C_{11}$ ether, as well as validate the accuracy of the fuel property predictions, a synthetic demonstration of the selected pathway was performed, as shown in FIG. 3. 4-butoxyheptane was targeted as a proof-of-concept molecule due to its availability from the ketone and alcohol upgrading products of a butyric acid feedstock. Vapor-phase hydrogenation of butyric acid using a $Ru_3Sn_7/ZnO$ catalyst was utilized to produce the n-butanol. Vapor-phase ketonization of butyric acid using a commercial $ZrO_2$ catalyst was utilized to produce the 4-heptanone.

Figure 4:
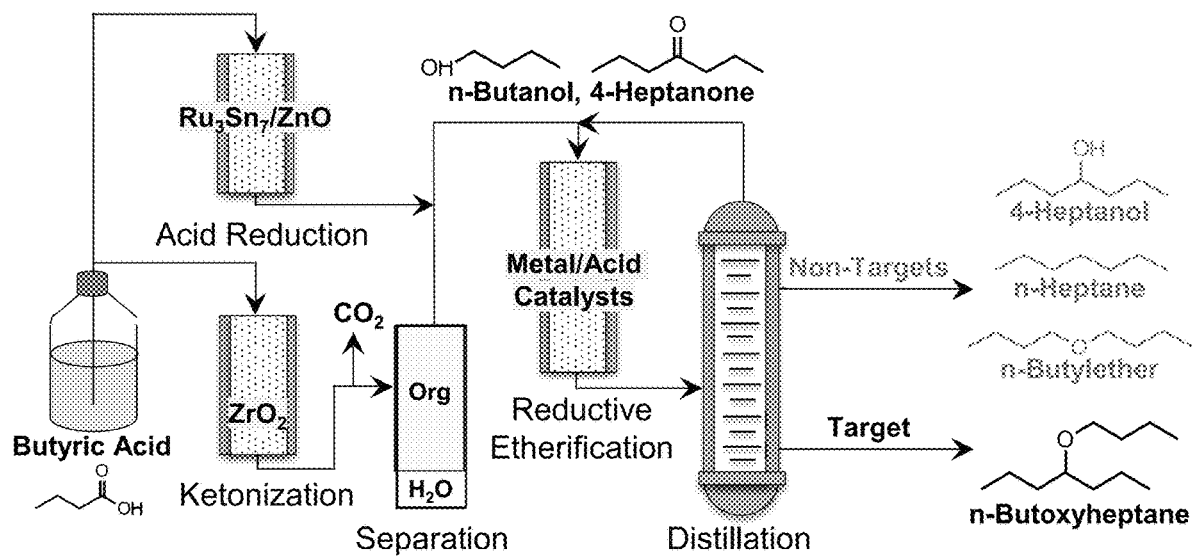
FIG. 4 illustrates a general flow diagram for completing hydrogenation, ketonization, and etherification reactions for producing, among other things, n-butanol, 4-heptanone, and 4-butoxyheptane, according to some embodiments of the present disclosure.

A general flow diagram for completing the hydrogenation, ketonization, and etherification reactions is shown in FIG. 4. A portion of carboxylic acids are converted to alcohols by catalytic hydrogenation, while the remaining portion of carboxylic acids are converted to ketones by catalytic ketonization. Ethers may then be produced from the alcohols and ketones by catalytic reductive etherification. Referring to FIG. 4, a butyric acid stream may be split into two parallel reaction streams. Key process parameters for the butyric acid to C11 ether portion of the process are outlined in Table 1 below. In some embodiments of the present disclosure, a first reactor may perform a gas phase ketonization reaction at 365° C. and atmospheric conditions over a $ZrO_2$ catalyst to produce 4-heptanone. The $CO_2$ produced may be separated via flash and a scrubber may be used to recover the 4-heptanone. Water may be separated from the 4-heptanone using a decanter. A second reactor may perform a C4 acid reduction reaction to n-butanol in the vapor phase using hydrogen at high pressure (25 atm) over a RuSn—ZnO catalyst.

Next, as described herein, the n-butanol and 4-heptanone may undergo a liquid phase etherification reaction at 190° C. and 1000 psi in the presence of hydrogen over a $Pd/NbOPO_4$ catalyst to produce 4-butoxyheptane. In addition to the reaction to produce 4-butoxyheptane, multiple side reactions are modeled. Some of these reactions are listed in Table 2 below. The effluent of the etherification reactor may be sent to a column, which separates out 4-butoxyheptane out of the bottom, with all other components exiting in the distillate stream. This stream may be sent to a decanter, yielding an organic phase, which may be sent downstream for further separations, and a water stream, sent to the wastewater treatment facility.

The organic stream from the decanter may be first sent to a molecular sieve dryer to remove the majority of the residual water, due to the presence of a ternary azeotrope between water, butanol, and heptane. The effluent from the dryer may be sent to a vacuum distillation column meant to separate out heptane. The distillate from this column may be made up of an azeotropic mixture of heptane and butanol. This stream may then be sent to a pressurized (30 psia) column, which shifts the azeotrope and allows for a pure heptane bottoms product, which serves as a gasoline-range blendstock. The distillate of this column may be recycled back to the vacuum column.

The bottom stream from the vacuum column may be sent to a series of distillation columns. The first column may separate butanol for recycling, while the second column may separate 4-heptanol for inclusion in the product blendstock. Finally, a mixture of 4-heptanone and DBE remains. This separation proves very difficult due to an azeotrope forming at about 0.4 mass fraction of DBE, which does not change significantly with pressure. This stream may be sent to a column, which produces a pure 4-heptanone bottoms stream for recycling and a distillate stream close to the azeotrope composition.

TABLE 1

Exemplary process parameters for 4-butoxyheptane production. Design Basis

| | |
|---|---|
| Butyric Acid Reduction | |
| Temperature | 265° C. |
| Pressure | 24.67 atm |
| Catalyst | RuSn—ZnO |
| WHSV: | 0.9 h$^{-1}$ |
| Ketonization | |
| Temperature | 365° C. |
| Pressure | 1 atm |
| Catalyst | ZrO$_2$ |
| WHSV | 6 h$^{-1}$ |
| Etherification | |
| Temperature | 190° C. |
| Pressure | 1000 psig |
| Catalyst | Pd/NbOPO$_4$ |
| WHSV | Dependent on case |

TABLE 2

Reaction stoichiometry for 4-butoxyheptane production.

| Reaction | Stoichiometry |
|---|---|
| Butyric Acid Reduction | Butyric Acid + 2 H$_2$ → n-Butanol + H$_2$O |
| Ketonization | 2 Butyric Acid → 4-Heptanone + CO2 + H$_2$O |
| Etherification | n-Butanol + 4-Heptanone + H$_2$ → 4-Butoxyheptane + H$_2$O |
| Etherification side reaction | 2 n-Butanol → n-Butyl Ether + H$_2$O |
| Etherification side reaction | 4-Heptanone + H$_2$ → 4-Heptanol |
| Etherification side reaction | 4-Heptanol + H$_2$ → Heptane + H$_2$O |

The etherification reaction of n-butanol and 4-heptanone to 4-butoxyheptane was initially investigated in a batch reactor using purchased compounds. The reaction can occur in the presence of metal and acid functionalities, for example palladium (about 5% loading Pd/C) with Amberlyst-15 (Brønsted acid) to catalyze reductive etherification through a ketal intermediate. A set of reaction condition screenings showed conversion of 4-heptanone as high as 87% with ether yields reaching above 50% and 60% selectivity. For example, in some embodiments of the present disclosure, n-butanol was reacted with 4-heptanone to produce 4-butoxyheptane using excess n-butanol at a ratio of n-butanol to 4-heptanone between about 2:1 and about 4:1, corresponding to 0.125-1 mol % 1:1 Pd/C/Amberlyst catalyst mixture (i.e. a concentration between 0.125 and 1.0 mol % Pd on a carbon support, with the supported carbon mixed with Amberlyst at a 1:1 weight ratio), at a hydrogen pressure between about 10 bar and about 60 bar H$_2$, a reaction temperature between about 50° C. and about 120° C., and at a residence time between 2.5 hours and 10 hours.

Figure 5:
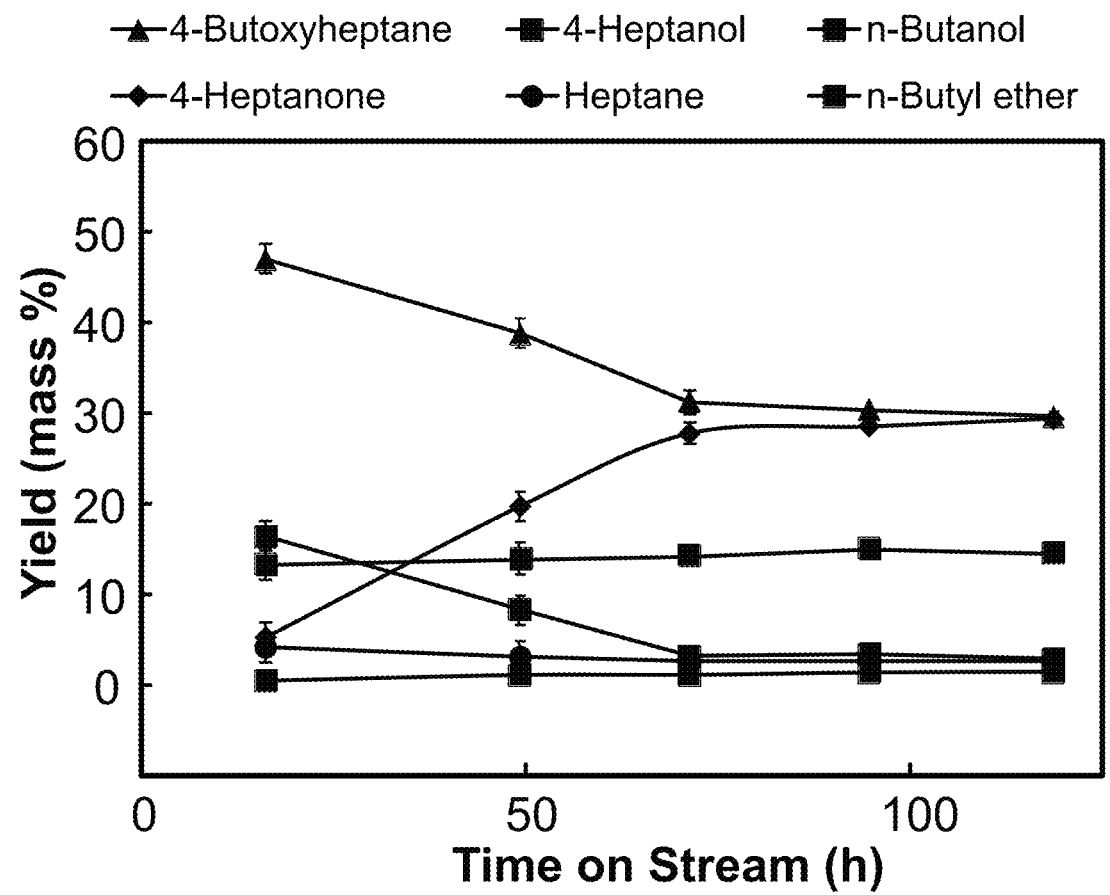
FIG. 5 illustrates time-on-stream data showing etherification reactants and products over a 118-hour time-frame where the reaction was performed in a trickle bed reactor, according to some embodiments of the present disclosure.
Figure 6:
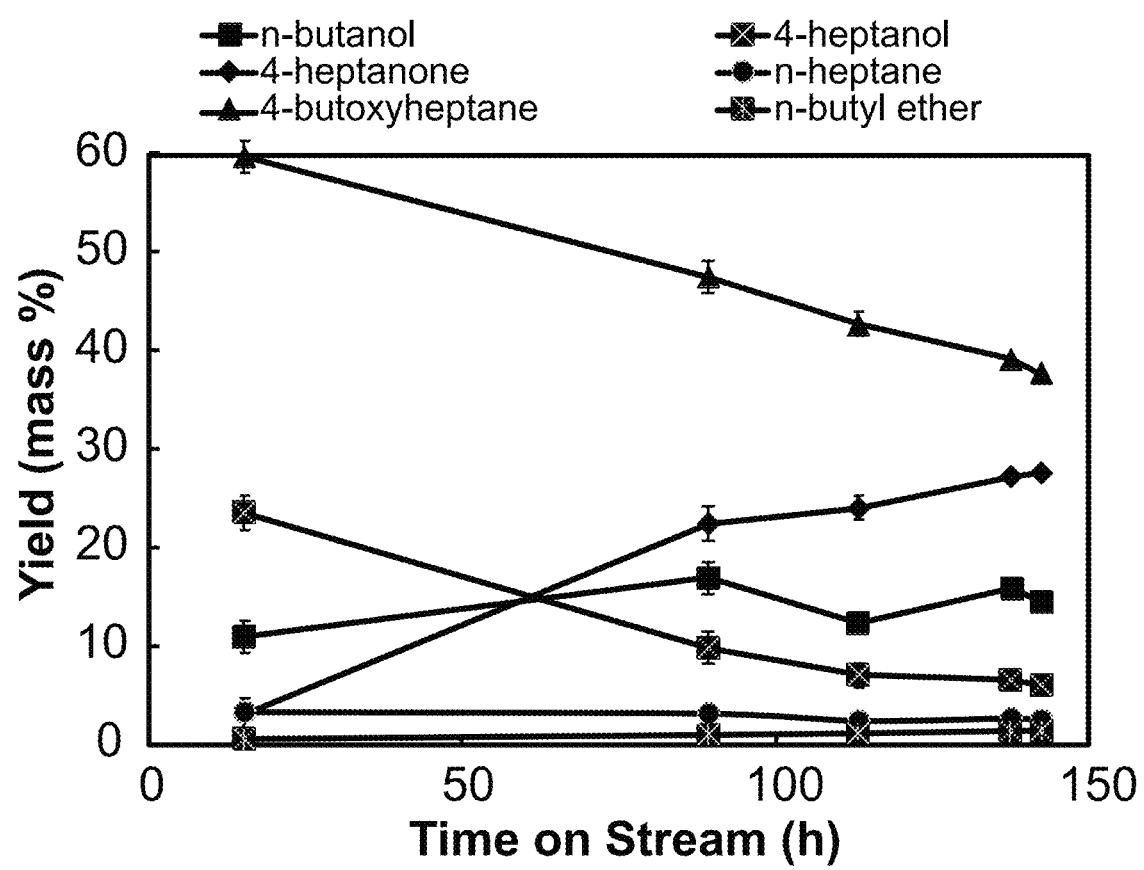
FIG. 6 illustrates time-on-stream data for the etherification n-butanol and 4-heptanone, utilizing ground Pd/C and Amberlyst-15 catalysts in the presence of hydrogen ($H_2$) to produce 4-butoxyheptane, according to some embodiments of the present disclosure.

The etherification reaction of n-butanol and 4-heptanone to 4-butoxyheptane was also tested in a trickle bed flow reactor, targeting maximum ether production using the optimum conditions as determined by the batch experiments, thus demonstrating the continuous production of the target ether, 4-butoxyheptane, using a scalable manufacturing process. FIGS. 5 and 6 shows representative time-on-stream data for the reductive etherification over ground Pd/C and Amberlyst-15 catalysts in hydrogen. At a flowrate of 0.25 mL/min of 1:1 n-butanol to 4-heptanone reactants (120° C., 1000 psig H$_2$, 2.2 g Pd/C, 6.6 g Amberlyst-15) over approximately 142 hours, liter-scale quantities were fed producing 705 g of target ether overall (45.2 wt % yield, 73.7% selective to 4-butoxyheptane), as quantified by gas chromatography/PolyArc analysis, with 94% mass closure on average without significant gaseous losses. The successful scaled production to multi-liter quantities of ether, while confirming the potential conversion capability, additionally allowed for sufficient volume to be collected to enable comprehensive fuel property and compatibility experimental evaluation. By-products of both batch and continuous reactions of n-butanol and 4-heptanone to produce 4-butoxyheptane included 4-heptanol, as well as small quantities of heptane with n-butyl ether being detected only in the batch reactor experiments. n-butyl ether may be formed by heptanol reduction and n-butanol etherification, respectively.

Figure 7:
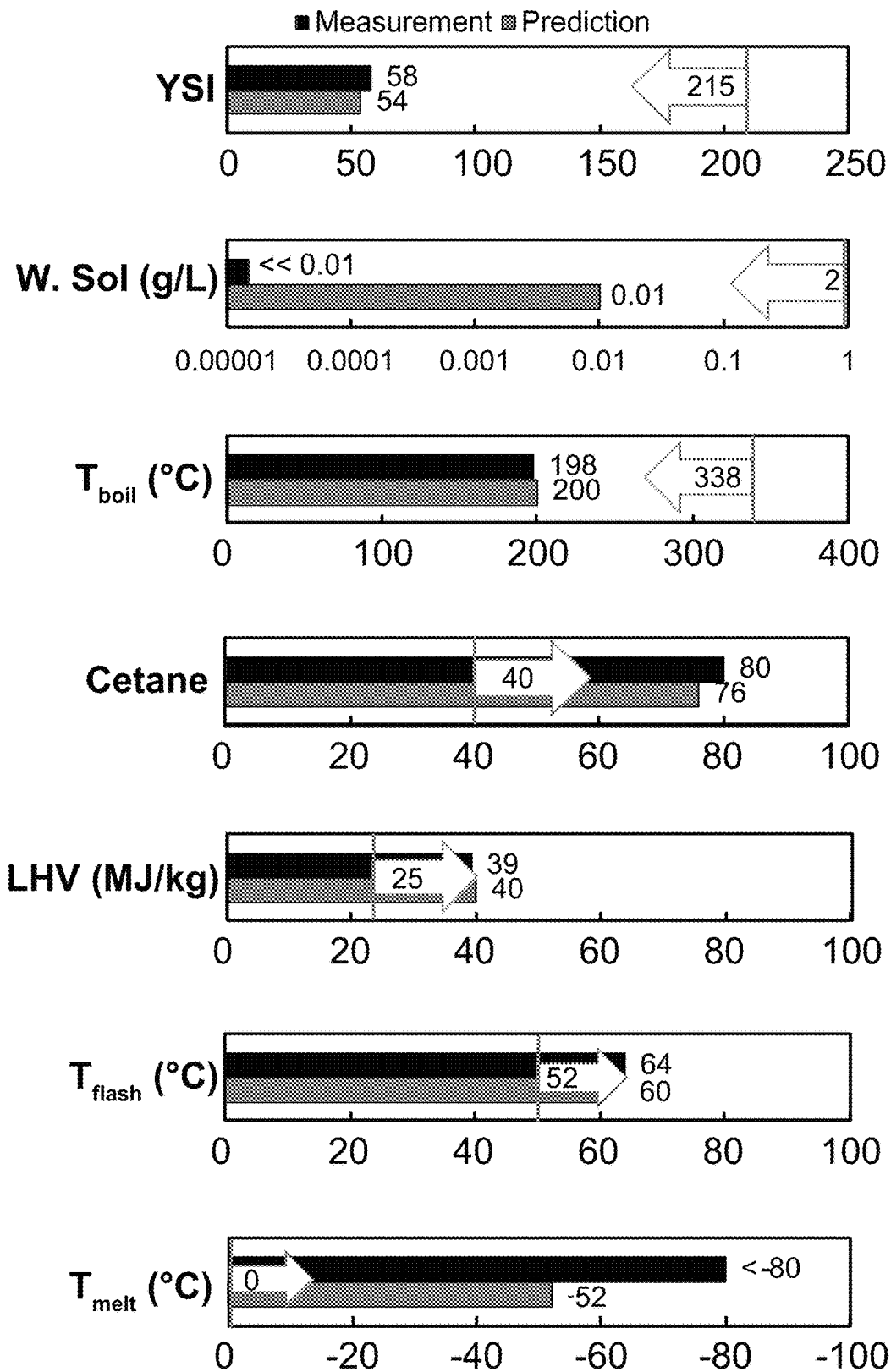
FIG. 7 illustrates fuel property predictions (lighter bar) compared with measured fuel properties (black bar) of a purified $C_{11}$ ether, according to some embodiments of the present disclosure. The performance-advantaged region for each fuel property is indicated by the arrow marked with the specific numerical criterion for diesel blendstocks.

Successful synthetic scale-up of the ether production process enabled fuel property testing in order to evaluate the promise of bioderived ethers as an advantaged fuel and/or blendstock. FIG. 7 provides a visual summary of fuel property measurements compared with mathematically modelled predictions, with criteria illustrated with an arrow containing the numerical cut off for a high-performance diesel fuel. For all criteria except water solubility, melting point, and flashpoint, the measured metrics obtained from the experimentally derived ether, 4-butoxyheptane, were comparable to the predicted metrics. Where predictions and measurements showed large discrepancies, the measured properties actually proved better than anticipated from predictions. For instance, the predicted flashpoint (55° C.) of the 4-butoxyheptane was very near the minimum cut off criterion, while the measured result was 64° C. Similarly, the water solubility was significantly lower than expected, and well within the cut off of 2000 mg/L. These metrics, along with a very low YSI confirmed by measurement, address the preliminary checks for health and safety-related characteristics of the purified blendstocks. Performance metrics such as cetane number (CN) and lower heating value (LHV) were confirmed by measurement to verify the target compound, 4-butoxyheptane, as having high-performance diesel characteristics, with values of 80.0 and 39.2 respectively.

Figure 8A:
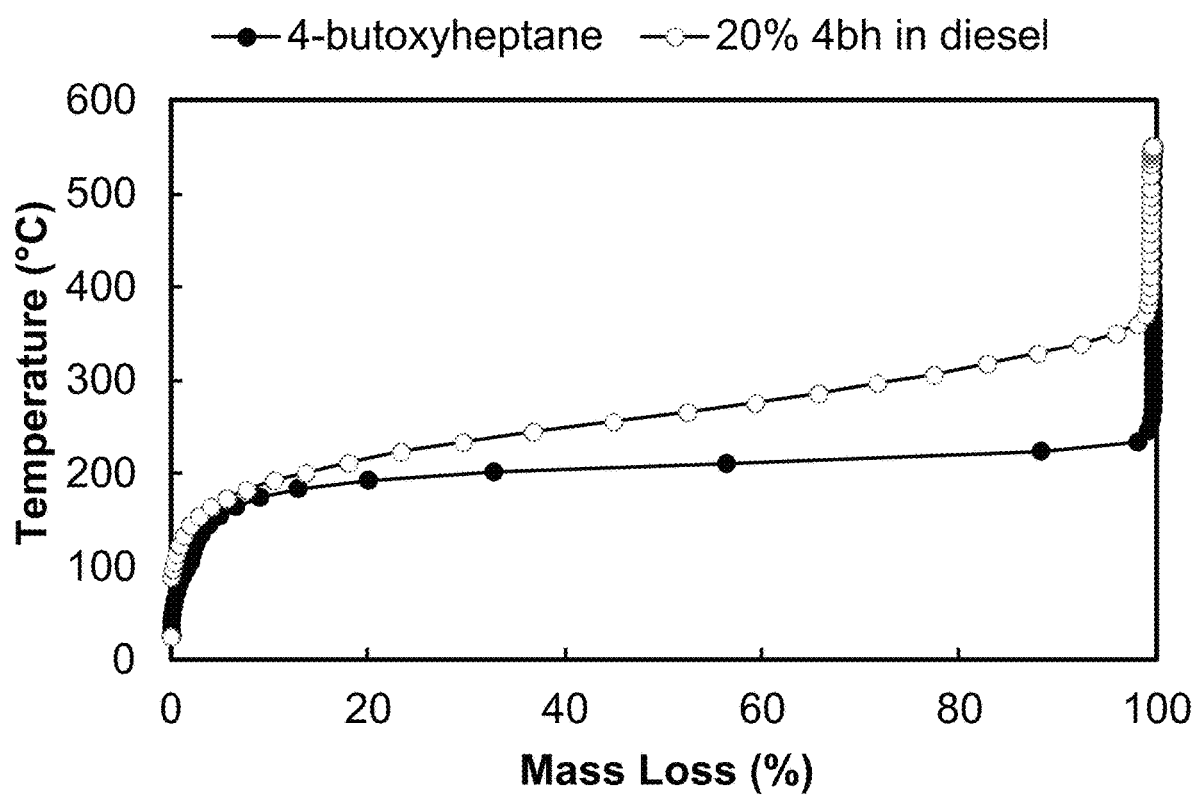
FIG. 8A illustrates TGA data showing mass loss upon temperature ramp, according to some embodiments of the present disclosure.
Figure 8B:
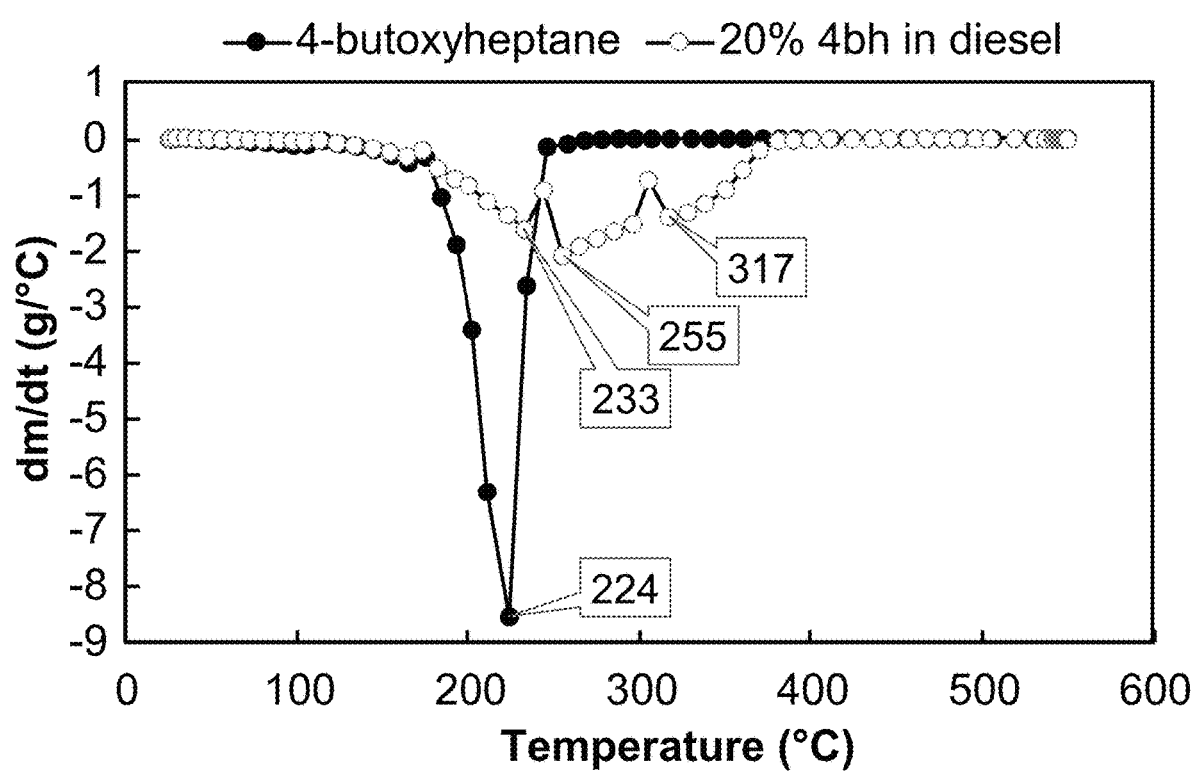
FIG. 8B illustrates, for the TGA data shown in FIG. 8A, the change in mass over temperature revealing multiple boiling points of the diesel blend, according to some embodiments of the present disclosure.
Figure 9:
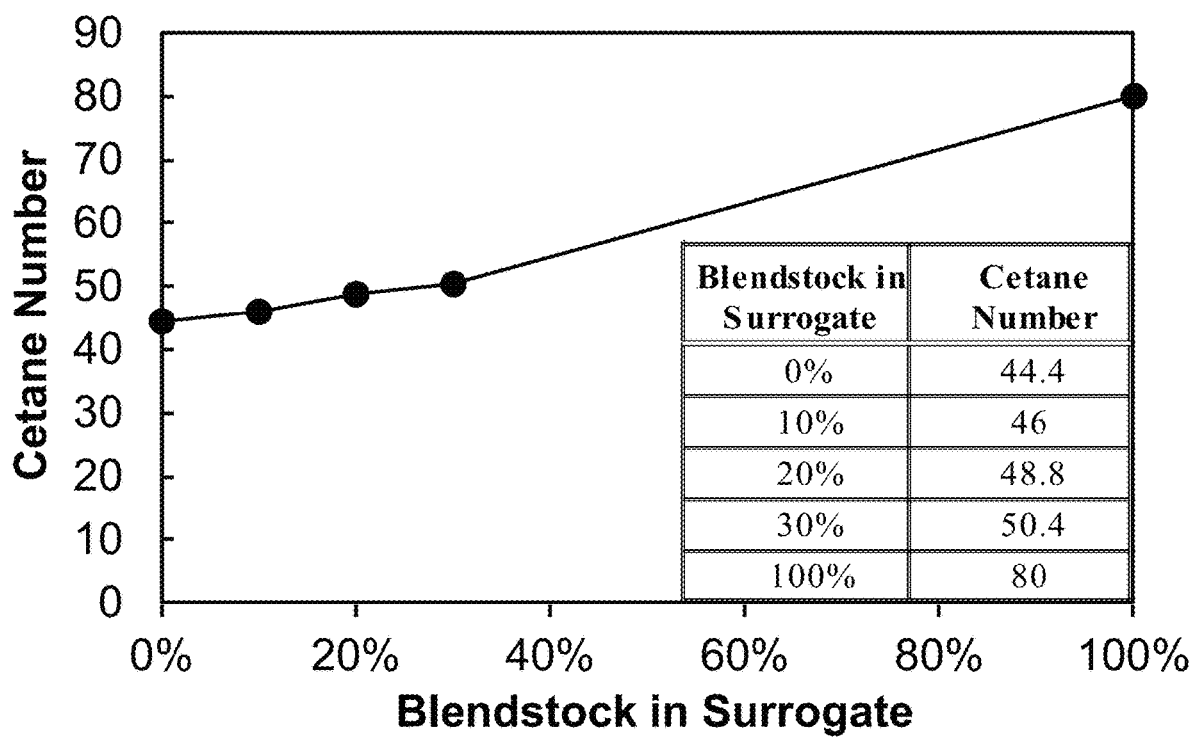
FIG. 9 illustrates cetane numbers of various blend compositions of ether blendstock in a simple 7-component diesel surrogate, according to some embodiments of the present disclosure. As used herein "diesel surrogate" refers to a simple mixture of hydrocarbons designed to emulate the fuel properties of complex diesel fuel

The fuel property testing of the purified ether, 4-butoxyheptane, both alone and in a diesel blend indicate 4-butoxyheptane's promise for use as a diesel blendstock. In order to further validate the viability for use of the ether as a diesel blendstock, fuel property measurements of the blendstock in diesel were also made and compared to the characteristics of the base diesel high performance fuel criteria. Table 3 summarizes important base diesel and blend (20 vol % blendstock in diesel) properties, and also quantifies the percent change in base diesel properties upon incorporation of the blendstock where applicable. High performance fuel (HPF) criteria are summarized in the far-right column of the table and appear green where criteria are met. These data show that the melting point, cloud point, and boiling point (from TGA, see FIGS. 8A and 8B) of the base diesel were all decreased upon blending with the ether, a favourable direction for their individual HPF criteria. LHV decreased by 5 to 40 MJ/kg. Cetane number was slightly improved and was observed to blend linearly between 10 and 30 vol % (see FIG. 9). Flashpoint stayed essentially the same within measurement error. The blend showed only 4E-6 g/L extraction of the ether into water, indicating that the ether maintained a low water solubility after incorporation with diesel. Interestingly, the 20 vol % addition of ether had the effect of significantly reducing the YSI of the base diesel from 215 to 173.

TABLE 3

| Property | Base Diesel[a] | Blend[b] | HPF Criteria[c] |
|---|---|---|---|
| $T_{cloud}$ (° C.) | −9.7 | −11.4 | <0 |
| $T_{boil}$ (° C.)[d] | 333 | 268 | <338 |
| $T_{flash}$ (° C.) | 61 | 62 | >52 |
| LHV (MJ kg$^{-1}$) | 45.3 | 40 | >25 |
| v (cSt) | 2.66 | 2.12 | 1.9-4.1 |
| CN[e] | 44.4 | 48.8 | >40 |
| Water Sol (g/L) | Low | Low[f] | <2 |
| YSI | 215.1 | 173.1 | Low |

[a]See Table 4 for additive-removed diesel properties
[b]20 vol % blend ether in base diesel
[c]All target criteria were met.
[d]Average of multiple BPs from TGA of diesel/ether blend (see FIG. 8)
[e]20% blend in surrogate diesel - see FIG. 8) for CN at other blend compositions
[f]A 20 vol % blend of ether in diesel showed 4E-6 g/L extraction of the ether into water, indicating maintained low water solubility after blending In order to get an idea of the potential biodegradability and environmental impact of the exemplary ether, 4-butoxyheptane, a quantitative structural activity response technique (QSAR) was employed to complement the initial water solubility check. This technique essentially assesses the impact of breakdown products of complex molecules and returns a collation of the impact as a value. According to EPI Suite and EPA TEST analytics, in the event of an accidental environmental release, 92% of the 4-butoxyheptane would partition into the air column and 7.5% would remain in the soil, and given the experimentally verified low solubility of the target ether it is unlikely that it will migrate from the soil into water supplies.

The next important consideration is that of safety and fuel quality upon storage of the novel blendstock. Oxidation stability of 4-butoxyheptane was examined experimentally. Two distinct characterizations were performed regarding oxidation potential during storage. The first utilized a rapid small-scale oxidation test (RSSOT) using a PetroOxy instrument to determine induction time, which indicates the potential for a fuel to oxidize during storage, which may result in quality degradation from formation of low molecular weight acids and insoluble polymers. Neat ether was found to have an induction period of about 23 minutes, but upon addition of 100 ppm of an antioxidant (butylated hydroxytoluene, BHT), it achieved stability above the 60-minute requirement for HPF diesel fuels.

TABLE 4

| Property | Measurement | ASTM Method |
|---|---|---|
| Flash Point (° C.) | 61 | D93 |
| Water and Sediment (° C.) | <0.005 | D2709 |
| Water (μg/g) | 37 | D6304 |
| Distillation Temp, T90 (° C.) | 335 | D86 |
| Viscosity at 40° C. cSt | 2.663 | D445 |
| Ash (mass %) | <0.001 | D482 |
| Sulfur (μg/g) | 6.2 | D5453 |
| Copper Strip Corrosion | 1A | D130 |
| Aromatics (vol %) | 31.6 | D1319 |
| Cetane Number (ICN) | 46.8 | D8183 |
| Carbon Residue (mass %) | 0.08 | D524 |
| Lubricity (μm) | 520 | D6079 |
| Conductivity (pS/m) | 1 | D4308 |
| Oxidation Stability (min) | 68 | D7545 |
| Total Acid Number (mg KOH/g) | 0.08 | D664 |
| Peroxide Value (mg/kg) | 1 | AOCS Cd 8b-90 |
| Cloud Point (° C.) | −9.7 | D5773 |

In addition, in some embodiments of the present disclosure, phosphated metal oxide materials were shown to efficiently catalyze the etherification reaction between n-butanol and 4-heptanone to form 4-butoxyheptane. Single-phase solid catalysts synthesized from palladium deposition onto phosphated metal oxides were assessed as a possible replacement for co-mixed acid and metal systems. The acidity, hydrophobicity and long-term catalytic stability of these materials were also evaluated to demonstrate the applicability of water-tolerant solid acid catalysts for the reductive etherification reaction.

Figure 10:
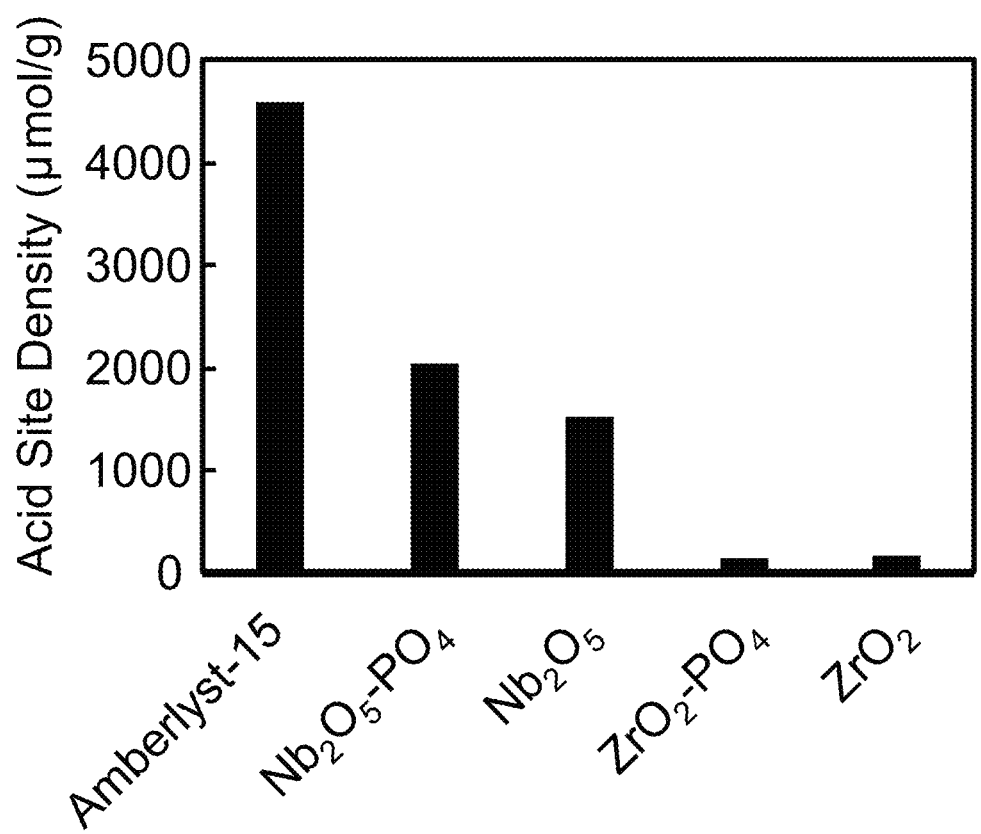
FIG. 10 illustrates $NH_3$-TPD acidity measurements of catalysts described herein, according to some embodiments of the present disclosure.
Figure 11:
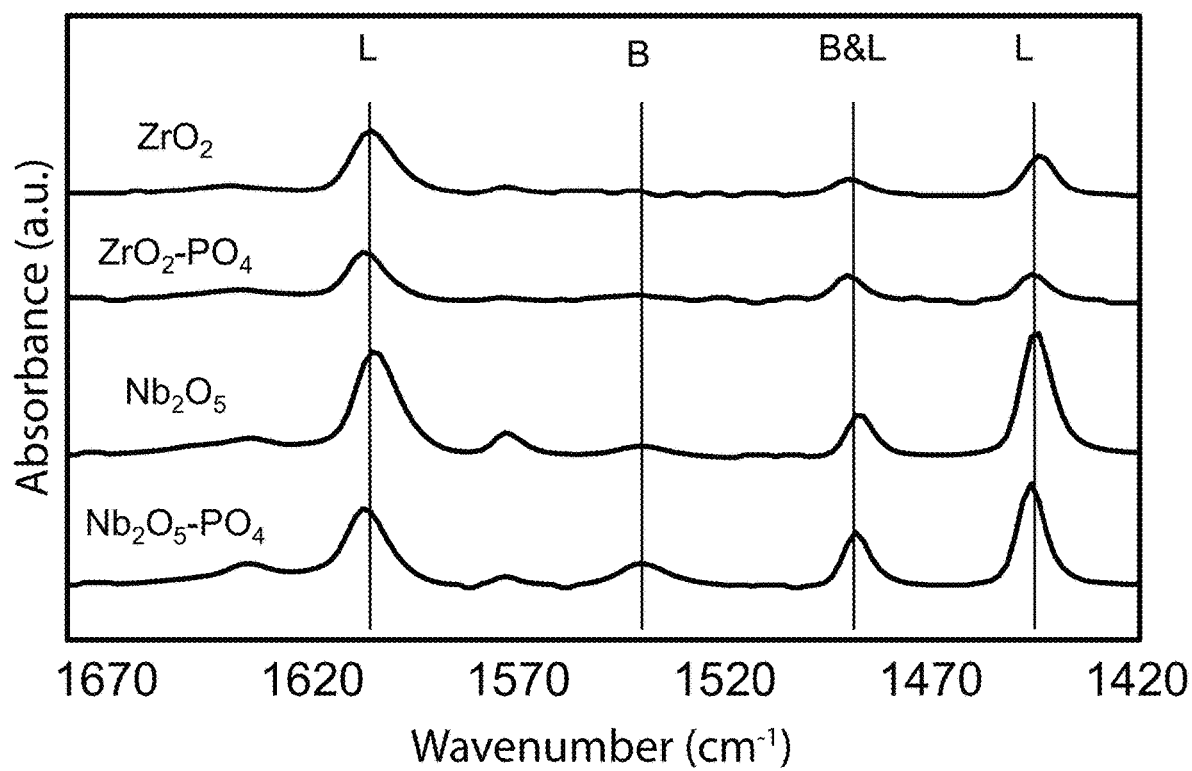
FIG. 11 illustrates pyridine-DRIFTS spectra of metal oxide precursors and phosphated solid acid catalysts, according to some embodiments of the present disclosure. Brønsted (B) and Lewis (L) acid site peaks are labelled.

The reductive etherification reaction can be catalyzed by a dual metal-acid system with palladium acting at the surface to stabilize hydrogen and facilitate reduction of intermediate compounds. Materials with high densities of Brønsted acid sites may be employed as the second component but these may readily adsorb the water produced by etherification, which may lead to reduced product yields over time. Utilization of water-tolerant solid acid materials with higher hydrophobicity and/or lower Brønsted/Lewis acid ratios relative to total acidity may show improved long-term stability by avoiding this undesirable adsorption of water. To determine the effect of phosphating and calcinating the metal oxides on the total acid site densities, $NH_3$-TPD measurements of the precursors and phosphated solid acids in water were performed and the results are shown in FIG. 10. Niobic acid ($Nb_2O_5$) showed an improvement in the acid site density after phosphating and calcinating ($Nb_2O_5$—$PO_4$) from 1500 to 2057 μmol/g. But these values were lower than the commonly utilized resin Amberlyst-15 (A-15) with an acidity value of 4600 μmol/g. Meanwhile, the acid site densities of both zirconia samples were an order of magnitude lower, exhibiting values of only 154 μmol/g for the phosphated sample ($ZrO_2$—$PO_4$) and 163 μmol/g for the calcined-only sample ($ZrO_2$). While the polymeric resin exhibits exclusively Brønsted acidity from sulfonic acid groups, the surfaces of metal oxides are more complicated and Pyr-DRIFTS measurements were performed to evaluate these samples. As shown in FIG. 11, the corresponding peaks for Brønsted (B) and Lewis (L) acidity vary for the different metal oxide samples and the relative amounts of each were determined by integrating the peaks at 1445 (L) and 1540 (B) cm$^{-1}$. Depositing phosphate groups onto the surfaces increased the ratio of Brønsted acidity for both metal oxides and the overall order of increasing Brønsted/Lewis ratio was: $ZrO_2$<$Nb_2O_5$<$ZrO_2$—$PO_4$<$Nb_2O_5$—

$PO_4$. These results suggest that the phosphating procedure creates a trade-off effect from the viewpoint of favoring Lewis acidity due to an increased total acidity and Brønsted/Lewis acid ratio. However, the hydrophobicity is also an important factor for imparting resistance of these materials to inhibitive water adsorption. See Table 6 for more details.

Two water adsorption measurements were performed on the solid acid catalysts samples to evaluate hydrophilicity. Thermogravimetric analysis measurements of water content after dosing in a saturated water chamber are shown in Table 5. The phosphated niobic acid sample showed a water content 7-fold lower than Amberlyst-15. Compared to a decrease in acid site density of only 2.2-fold between these two catalysts, this suggests a possible opportunity to optimize reaction efficiency as a water-tolerant solid acid catalyst by increasing acidity with milder changes in hydrophobicity. Zirconia showed negligible amounts of water on the surface of both the precursor and phosphated catalyst samples, but the acidity values were also an order of magnitude lower than the niobic acid and Amberlyst catalyst samples.

TABLE 5

| Catalyst | Water Content (wt %) |
| --- | --- |
| Amberlyst-15 | 21.95 |
| $Nb_2O_5$—$PO_4$ | 3.18 |
| $Nb_2O_5$ | 1.15 |
| $ZrO_2$—$PO_4$ | 0.12 |
| $ZrO_2$ | 0.09 |

Figure 12:
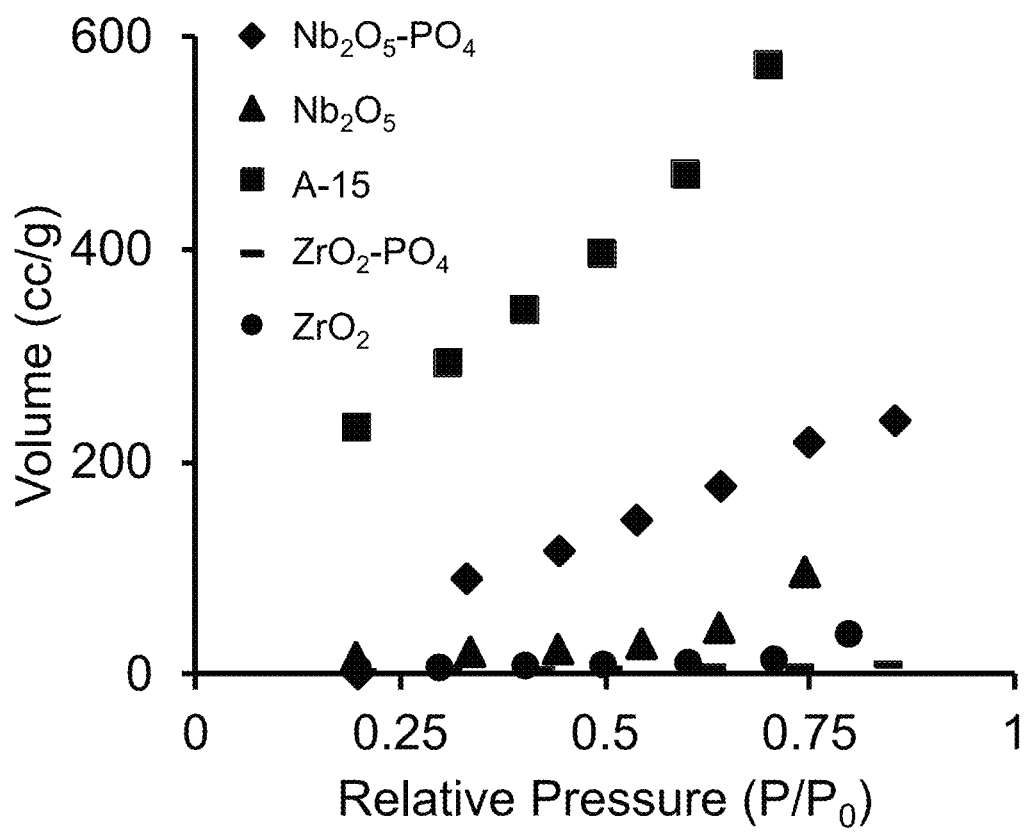
FIG. 12 illustrates water adsorption isotherm measurements from solid acid catalyst samples at 18° C., according to some embodiments of the present disclosure.

The $H_2O$ adsorption isotherms were also measured at several partial pressures of water vapor for A-15 and the same metal oxide samples (see FIG. 12). The same trend in water adsorption was seen using this technique, confirming the relative hydrophobicity for the various solid acid catalyst options. The hydrophobicity and acidity data for these catalysts is promising for water-tolerant acid catalysts, however, catalytic efficiency needs to be evaluated for the reductive etherification reaction to verify the applicability of these materials.

Figure 13:
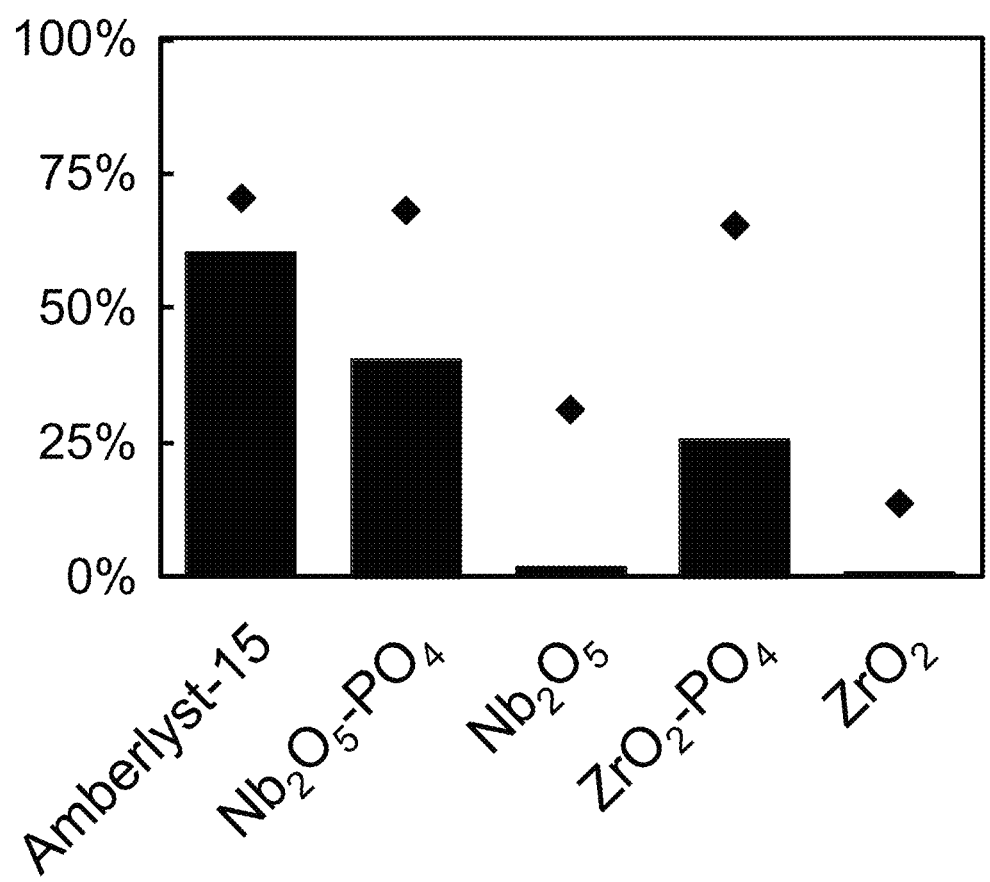
FIG. 13 illustrates batch reductive etherification yields (ether wt %-bars) and selectivity (diamond symbols) to ether formation (%) from 20 mL of equimolar n-butanol and 4-heptanone, 1000 psig of hydrogen gas after 5 hours for phosphated metal oxides, compared to mixtures of Pd/Carbon and phosphated metal oxides, according to some embodiments of the present disclosure.
Figure 14:
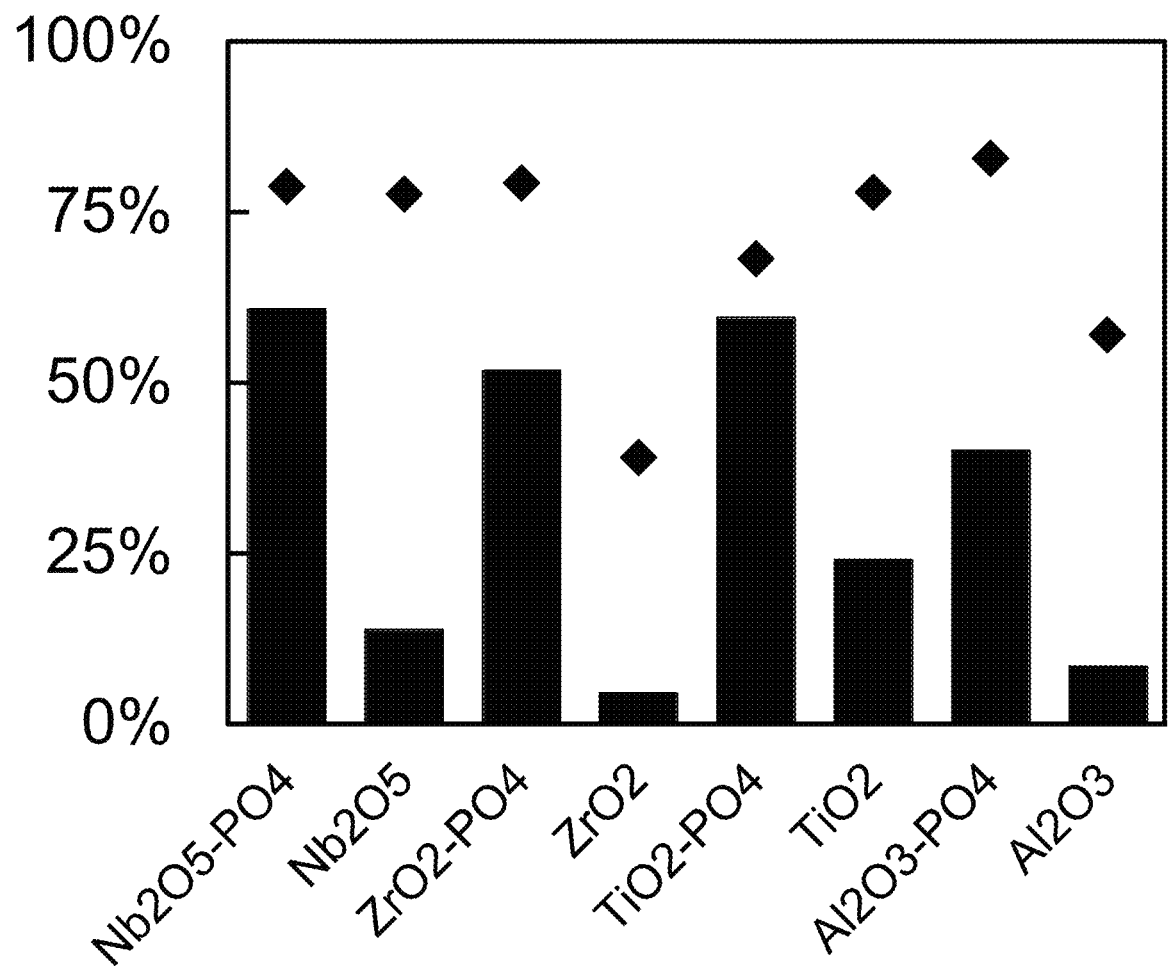
FIG. 14 illustrates batch reductive etherification yields (ether wt %-bars) and selectivity (diamond symbols) to ether formation (%) from 20 mL of equimolar n-butanol and 4-heptanone, 1000 psig of hydrogen gas after 5 hours for Amberlyst-15, compared to mixtures of Pd/Carbon and phosphated metal oxides, according to some embodiments of the present disclosure. Experiments performed at 190° C.

Batch reaction experiments are useful for preliminary screening of catalyst samples and reaction conditions. As described above, experiments were performed using equimolar amounts of n-butanol and 4-heptanone reactants (20 mL liquid volume) with 681 mg of solid acid catalyst (2.5 mol % for Amberlyst-15), 231 mg of 5 wt % Palladium-on-Carbon (0.13 mol %) and 1000 psig of hydrogen gas. As shown in FIG. 13, tests were first performed at the maximum allowable temperature for Amberlyst-15 (120° C.) for comparison of ether yields with phosphated metal oxide catalysts. At this temperature, lower yields were seen from the phosphated metal oxides relative to A-15, while only negligible product formation was seen from the bare metal oxides. Phosphated titania ($TiO_2$—$PO_4$) and phosphated alumina ($Al_2O_3$—$PO_4$) were also tested for catalytic efficiency at 190° C. in addition to the niobic acid and zirconia samples and those results are shown in FIG. 14. All four metal oxides showed an improvement in ether yield after the phosphating procedure at this temperature.

Figure 15:
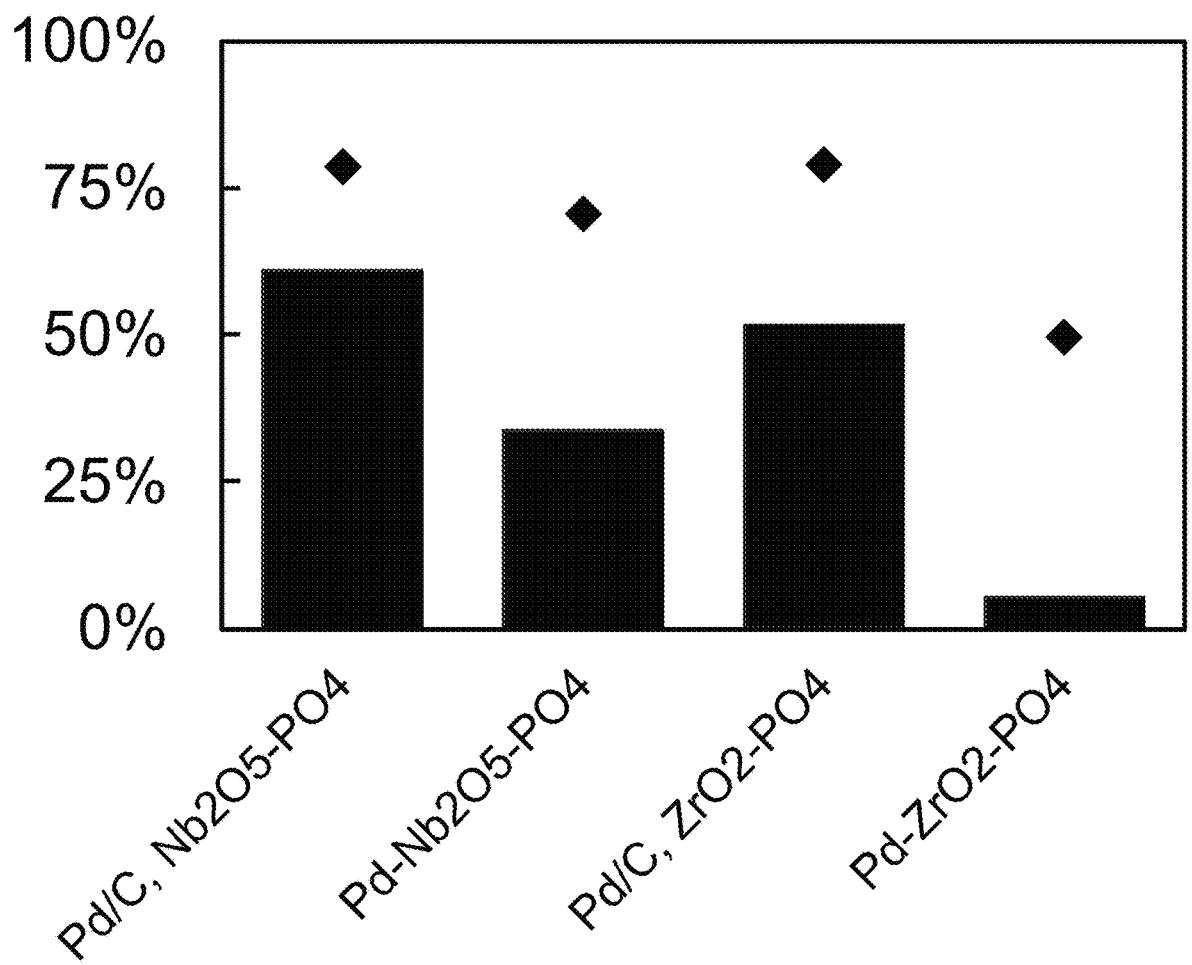
FIG. 15 illustrates batch reductive etherification yields (ether wt %-bars) and selectivity (diamond symbols) to ether formation (%) from 20 mL of equimolar n-butanol and 4-heptanone, 1000 psig of hydrogen gas after 5 hours for single-phase metal acid catalysts of Pd on phosphated metal oxides, compared to mixtures of Pd/carbon and phosphated metal oxides, according to some embodiments of the present disclosure.

Ether yields for the single-phase catalysts with Pd deposited onto phosphated metal oxides (Pd—$Nb_2O_5$—$PO_4$, Pd—$ZrO_2$—$PO_4$) are shown in FIG. 15. Lower yields were measured relative to the Pd/carbon mixtures (Pd/C, $Nb_2O_5$—$PO_4$ and Pd/C, $ZrO_2$—$PO_4$), however, further optimization is possible with increased Pd loadings and improved dispersion techniques such as strong electrostatic adsorption deposition techniques instead of incipient wetness. All three plots also show selectivity values for the formation of the ether product, but all experiments have shown selectivity values of more than 96% selectivity to diesel-grade molecules (4-butoxyheptane and 4-heptanol). The flash points of the other by-products (dibutyl ether and heptane) are insufficient for blending in diesel, but these compounds only form in small amounts under certain conditions. Overall, these results demonstrate increased yields with phosphated metal oxides for the reductive etherification reaction, but continuous flow reaction tests are more useful for the verification of long-term catalyst stability.

Figure 16:
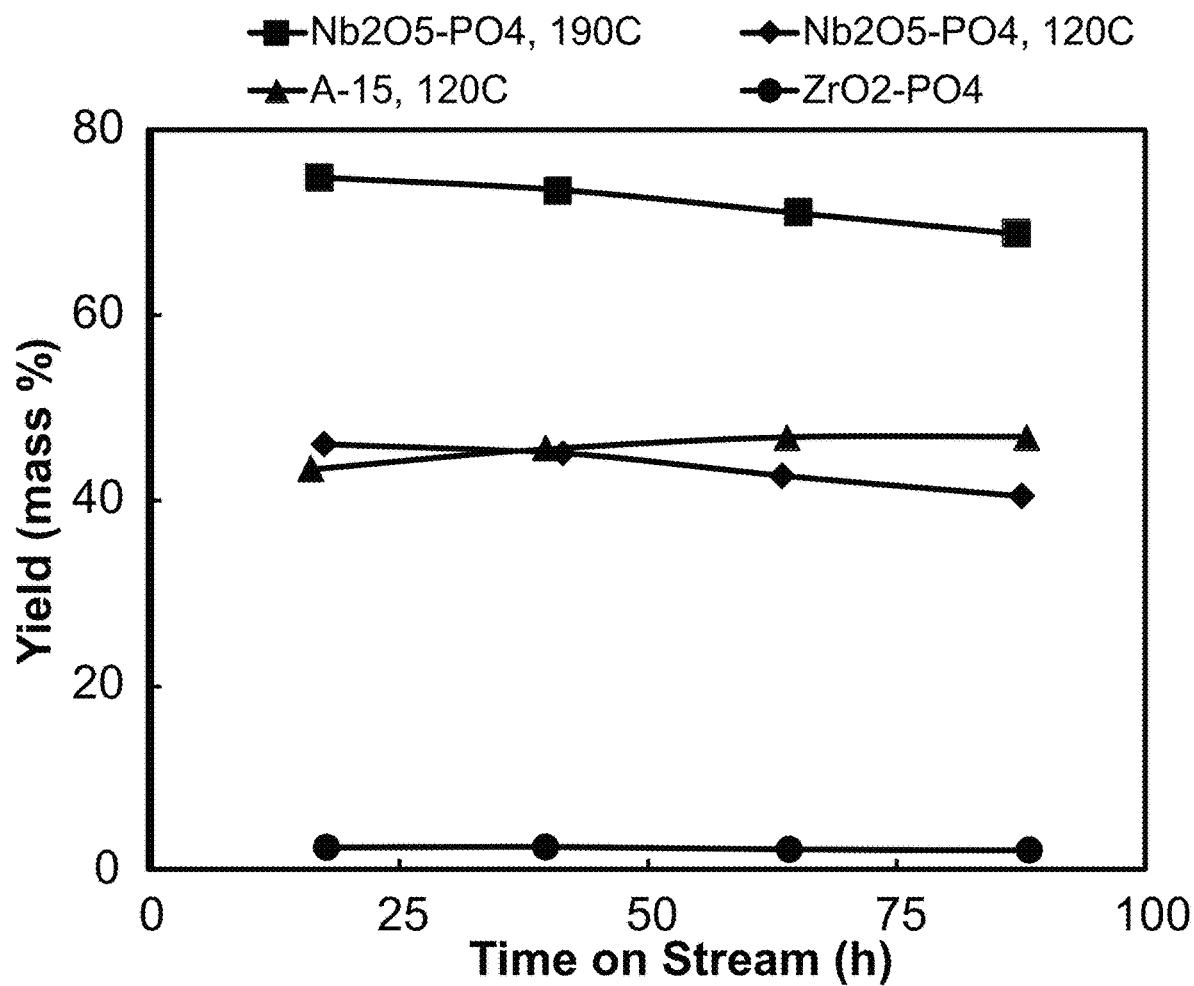
FIG. 16 illustrates continuous etherification yield of 4-butoxyheptane catalyzed using a mixture of palladium/carbon and various solid acids at 120° C. and 190° C., according to some embodiments of the present disclosure.

Continuous flow reaction tests are necessary to demonstrate transition to industrially relevant reaction systems with water-tolerant solid acid catalysts. For these experiments, reaction conditions were initially selected to match the highest yielding batch reaction results with Amberlyst-15, obtained from the previously described batch screening work. Phosphated niobic acid and phosphated zirconia were tested in a continuous flow reaction for etherification up to 90 hours and the ether yields are shown in FIG. 16. Phosphated niobic acid showed reasonable ether yields, 4-butoxyheptane, of approximately 40 wt % at 120° C. and an increased yield of about 66 wt % at an increased reaction temperature of 190° C. Both phosphated niobic acid samples showed drops in ether yield of 5 wt % over 90 hours suggesting a slow deactivation was still occurring. However, the phosphated zirconia sample yielded an average of only 7 wt % ether at 190° C. possibly due to the lower acid site density of this catalyst. The flow reactor test with A-15 as the acid catalyst at the maximum temperature (120° C.) showed an average yield of 42 wt %, close to the phosphated niobic acid result at the same temperature.

Figure 17:
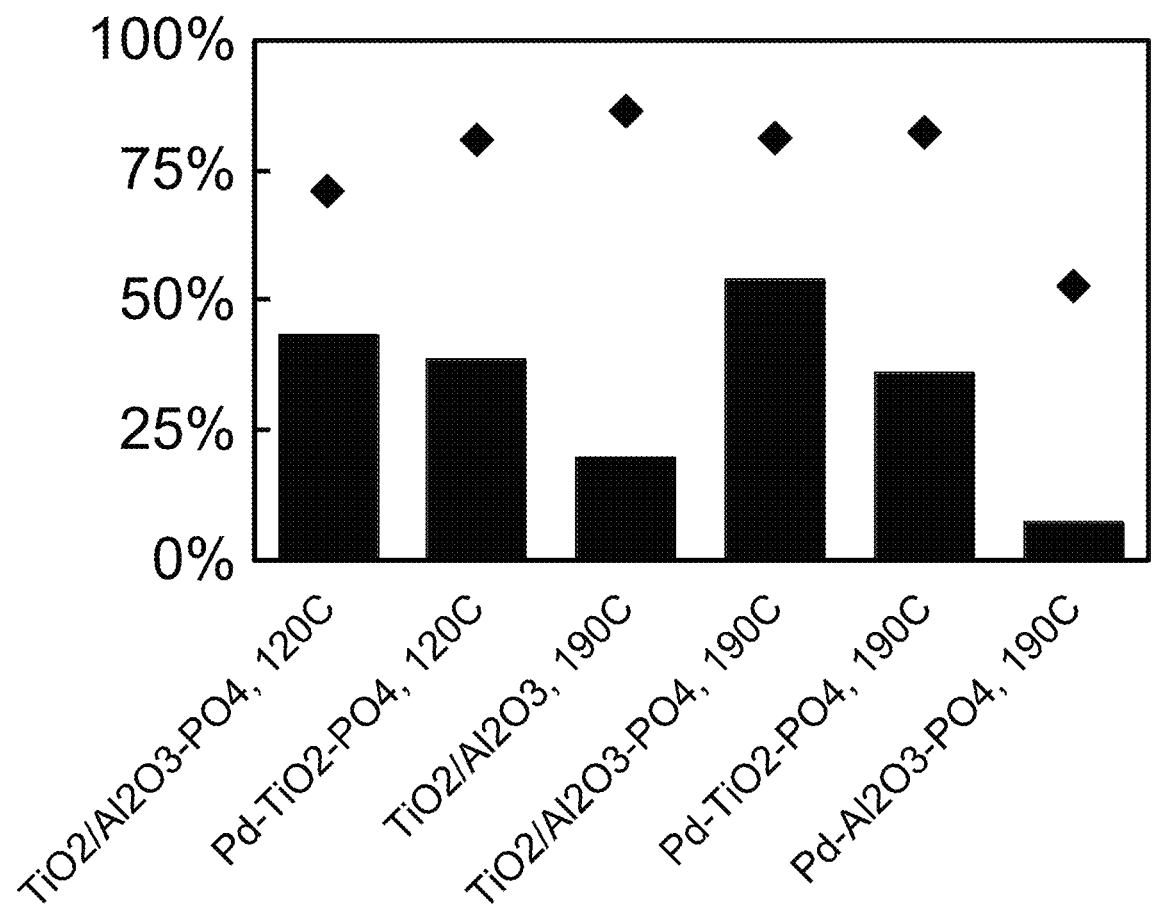
FIG. 17 illustrates a comparison of a phosphated titania/alumina solid acid to other materials for the production of 4-butoxyheptane, according to some embodiments of the present disclosure.

A phosphated titania/alumina solid acid material ($TiO_2$/$Al_2O_3$—$PO_4$) was prepared using the same phosphating procedure previously described on a sample of $TiO_2$ coated onto $Al_2O_3$ (20 cycles of atomic layer deposition). In addition, single-phase catalysts were synthesized through incipient wetness of palladium (2.5 wt % Pd, same procedure described previously) onto phosphated titania (Pd—$TiO_2$—$PO_4$) and phosphated alumina (Pd—$Al_2O_3$—$PO_4$). These catalyst samples were then screened with batch reaction testing (same procedure as described above, with one caveat; hydrogen pressure was lower at 825 psig instead of 1000 psig). The palladium-free phosphated titania-coated-alumina sample exhibited a higher yield of ether compared to the control without phosphorous loading (see FIG. 17). And this phosphated novel catalyst showed an improved yield and selectivity toward ether formation, 4-butoxyheptane, with an increase in temperature from 120° C. to 190° C. The single-phase catalysts of Pd deposited onto phosphated titania or alumina showed similar ether yields to the same solid acid materials mixed with Pd/carbon of FIG. 15. Overall, this demonstrates the feasibility of this phosphating procedure on titania and alumina-based solid acid materials and Pd-deposition on these supports for catalyzing the reductive etherification reaction.

Additional Catalyst and Reductive Etherification Studies:

Acidic metal oxide catalyst supports based on niobia and titania were synthesized and screened to provide an alternative to acidic resins used for reductive etherification. Titanium dioxide was obtained from Alfa Aesar, and both $Nb_2O_5$ and $NbOPO_4$ were obtained from CBMM. Catalyst supports were initially crushed, sieved, and calcined at 400° C. to before phosphating or testing catalytic performance. Characterization of the acidic metal oxide supports (see Table 6) determined higher surface area and acidity from the $TiO_2$ and $NbOPO_4$ base materials relative to $Nb_2O_5$. However, calcining niobic acid hydrate above 250° C. begins to increase the crystallinity of the material and subsequently decreases the surface area and acidity with the non-calcined $Nb_2O_5$ having a total acidity of 361 µmol $g^{-1}$. The phosphating procedure increased the surface area, total acidity and Brønsted acidity of the $Nb_2O_5$ and $TiO_2$ base supports.

Figure 19:
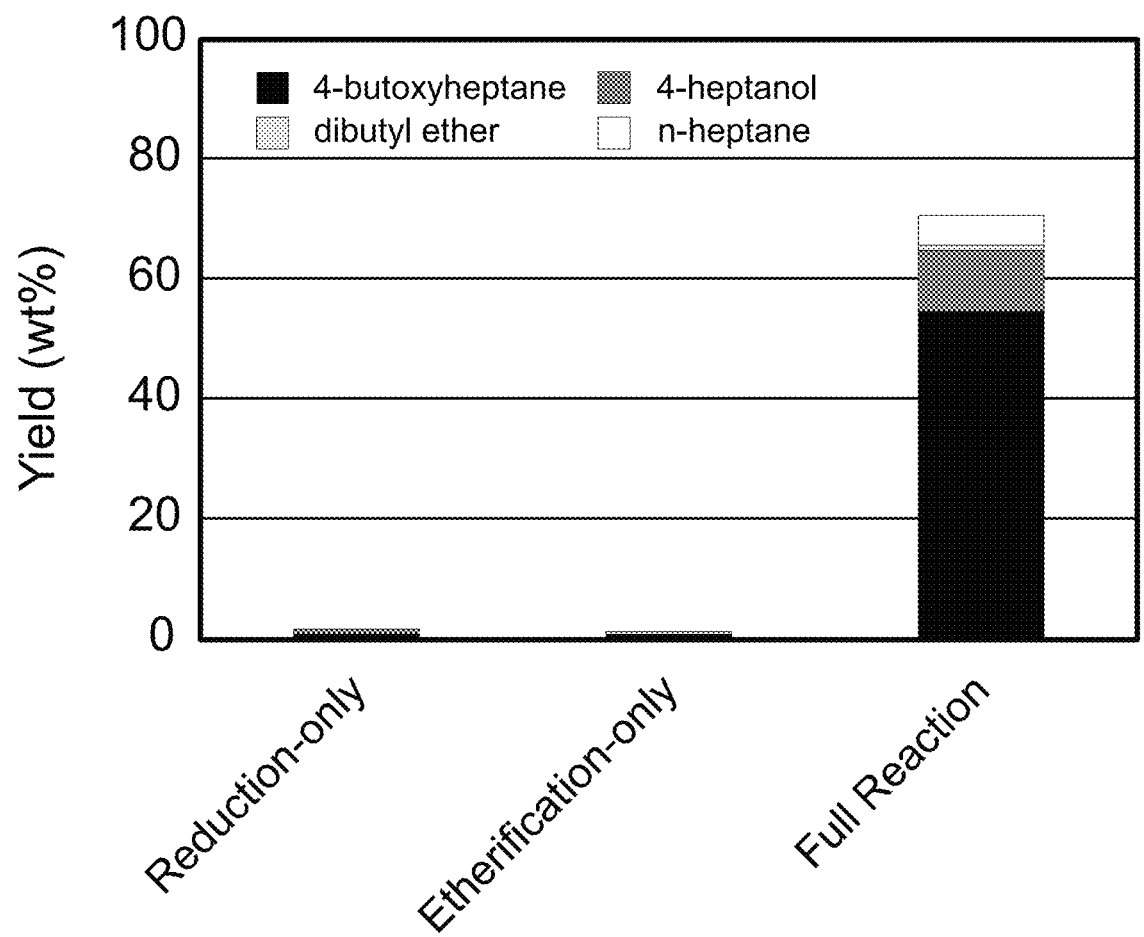
FIG. 19 illustrates batch reactor screening tests evaluating the reaction pathway shown in FIG. 3, according to some embodiments of the present disclosure.

The proposed catalytic reaction pathway in FIG. 3 was also supported through batch reactor tests that compared 4-heptanone reduction to direct etherification of n-butanol with 4-heptanol under identical reaction conditions (see FIG. 19). In the absence of an acid catalyst, trace amounts of 4-heptanol were formed (1±0.2 wt %), suggesting that ketone-to-alcohol reduction is not the initial reaction step leading to 4-BH formation. Likewise, the direct etherification reaction between n-butanol and 4-heptanol to form 4-BH only yielded 1±1 wt %. These results suggest that under the conditions tested, reductive etherification likely proceeds through the hemi-ketalization pathway (vertical reaction, FIG. 3), with the ketone reduction pathway (top horizontal reaction, FIG. 3) being significantly slower.

TABLE 6

Acidic metal oxide catalyst support material properties. *

| Metal Oxide Support | Surface Area ($m^2 g^{-1}$) | Pore Vol ($cm^3 g^{-1}$) | Total Acidity (µmol $g^{-1}$) | Bronsted Lewis Ratio |
|---|---|---|---|---|
| $Nb_2O_5$—$PO_4$ | 71 | 0.09 | 124 | 0.30 |
| $Nb_2O_5$ | 40 | 0.11 | 71 | 0.13 |
| $TiO_2$—$PO_4$ | 134 | 0.38 | 274 | 0.12 |
| $TiO_2$ | 107 | 0.36 | 215 | 0.00 |
| $NbOPO_4$ | 136 | 0.28 | 269 | 0.80 |

* Metal oxide supports were initially calcined at 400° C. for 5 hours in static air prior to characterization.

Figure 18:
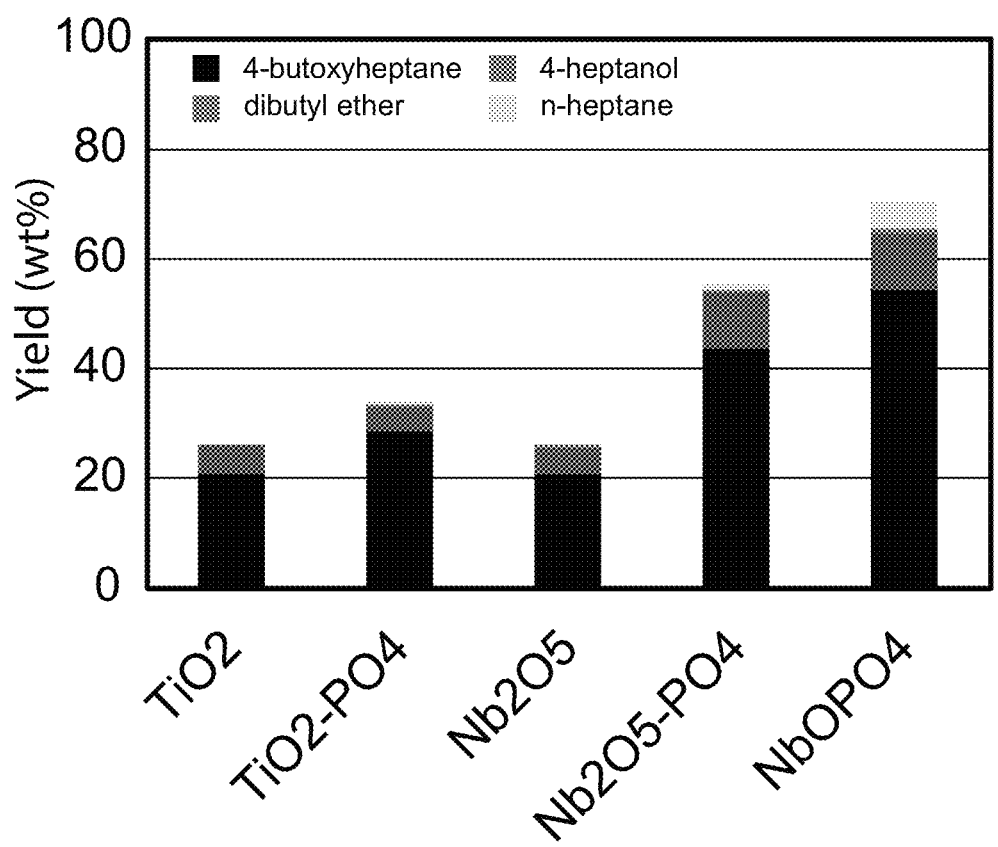
FIG. 18 illustrates acidic metal oxide support screening results using Parr batch reactors, as measured by yield of various target components, according to some embodiments of the present disclosure.

Next, acidic metal oxides were co-mixed with 5 wt % palladium-on-carbon (Pd/C) and screened for reductive etherification. 4-butoxyheptane (4-BH) was the target ether compound produced in a multi-batch Parr reactor system under 1000 psig $H_2$, at 190° C. with 800 rpm stirring, 20 mL equimolar n-butanol/4-heptanone, 230 mg of Pd/C and 680 mg of metal oxide for 1 hour. As shown in FIG. 18, the yield of 4-BH trended as $Nb_2O_5$<$TiO_2$<$TiO_2$—$PO_4$<$Nb_2O_5$—$PO_4$<$NbOPO_4$ and the full quantification dataset from batch screening is provided in Table 7. This trend is not fully accounted for by differences in Brønsted or total acidity, suggesting the multi-step reaction pathway may employ catalysis on both Brønsted and Lewis acid sites with a complex effect on rate and equilibrium.

Figure 20A:
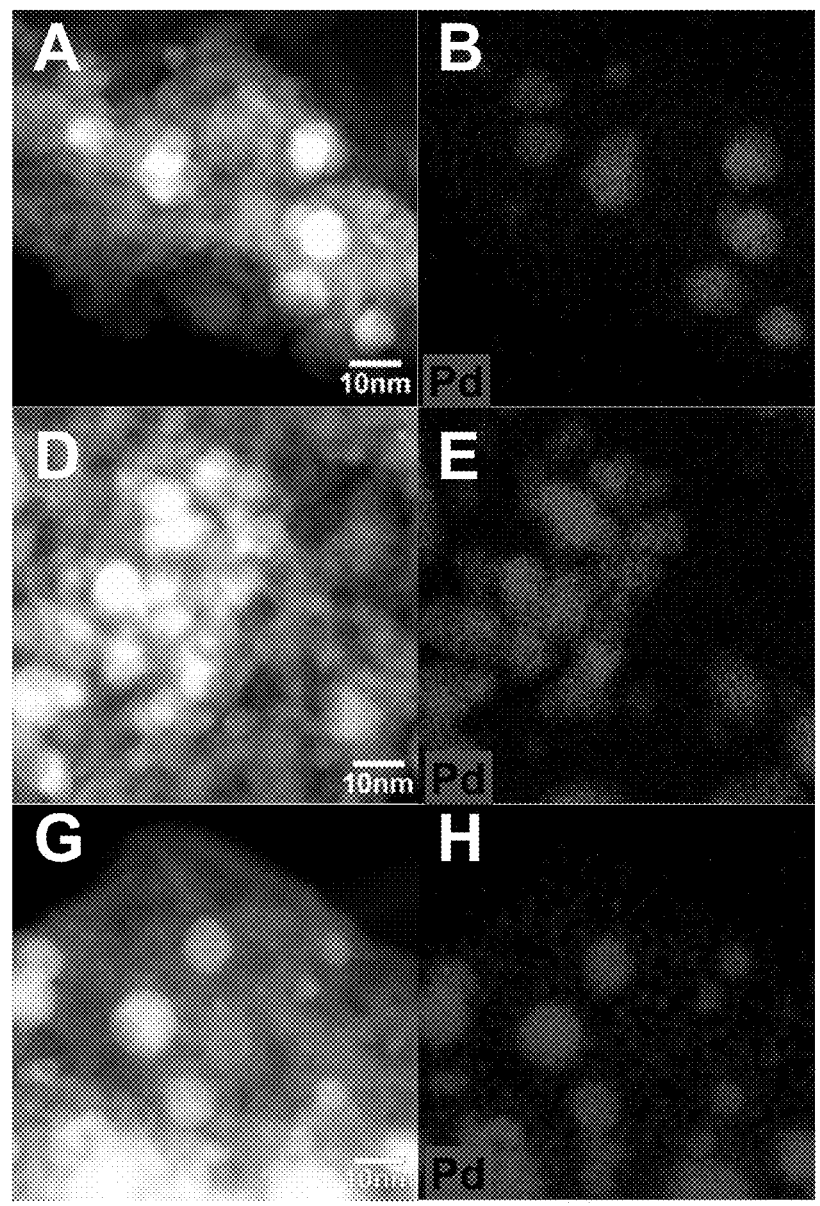
FIG. 20A illustrates characterization data of Pd/NbOPO$_4$ by STEM-EDS, according to some embodiments of the present disclosure. Samples include fresh catalyst (Panels A and B), spent catalyst after 117 h time-on-stream (Panels D and E), and regenerated catalyst after 4 simulated cycles (Panels G and H).
Figure 20B:
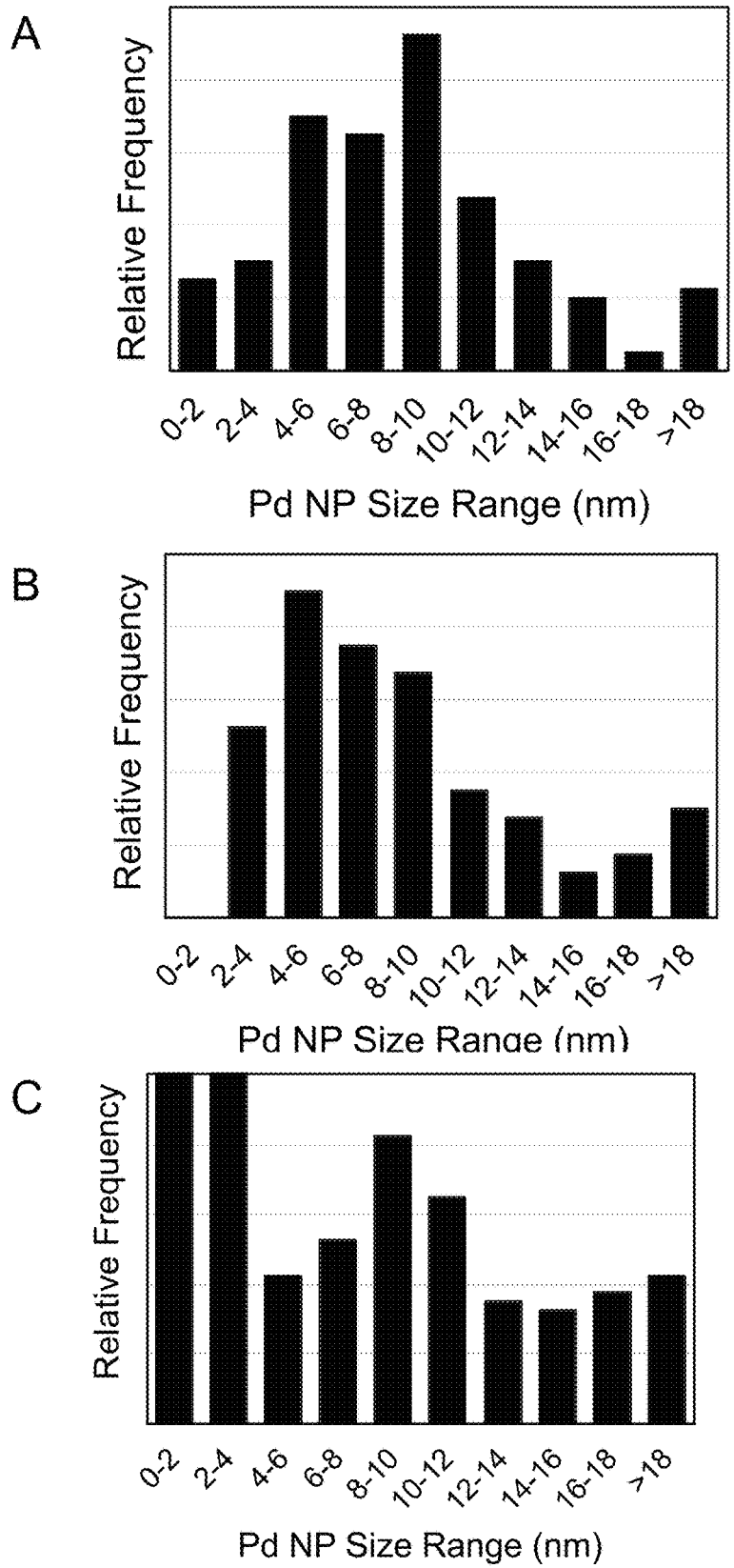
FIG. 20B illustrates particle size histograms of catalysts, for the same materials illustrated in FIG. 20A, according to some embodiments of the present disclosure. Samples include fresh catalyst (Panel A), spent catalyst after 117 h time-on-stream (Panel B), and regenerated catalyst after 4 simulated cycles (Panel C).

Single-phase catalysts were then prepared using the suite of phosphated acidic metal oxide supports. Palladium was deposited through incipient wetness impregnation, which can form metal crystallites on the scale of several nanometers in diameter. Single-phase catalysts were then prepared with 5 wt % Pd to determine the effect of metal loading on material properties (see Table 8). The loading of Pd on metal oxide was chosen to achieve similar conversion values to the Pd/C mixtures in the batch reaction screening tests. Minor changes in surface area and total acidity were seen for all catalysts after metal loading. CO chemisorption showed that Pd/$TiO_2$—$PO_4$ had approximately double the number of accessible Pd sites (35 µmol $g^{-1}$) relative to the niobium support materials (16 µmol $g^{-1}$). Pd metal crystallite sizes from XRD and Scherer analysis showed the same trend of increasing size from Pd/$TiO_2$—$PO_4$<Pd/$NbOPO_4$<Pd/$Nb_2O_5$—$PO_4$. However, STEM imaging of Pd/$NbOPO_4$ (see FIG. 20A) suggests a more complex mixture of particle sizes with the as-synthesized material having an average particle size of 10 nm and a broad standard deviation of 9 nm (see FIG. 20B).

TABLE 7

Carbon balance for batch reductive etherification tests over various catalysts.

| Catalyst | 4-Heptanone (wt %) | 1-Butanol (wt %) | 4-BH (wt %) | 4-Heptanol (wt %) | n-Butyl Ether (wt %) | n-Heptane (wt %) |
|---|---|---|---|---|---|---|
| Pd/C & $TiO_2$ | 44.2 ± 1.7 | 29.3 ± 3.0 | 21.2 ± 4.1 | 5.3 ± 0.6 | 0 | 0 |
| Pd/C & $TiO_2$—$PO_4$ | 46.0 ± 1.0 | 20.1 ± 0.3 | 28.4 ± 0.8 | 4.6 ± 0.4 | 0.7 ± 0.2 | 0.2 ± 0.0 |
| Pd/$TiO_2$—$PO_4$ | 50.3 ± 0.8 | 22.6 ± 0.2 | 19.4 ± 0.6 | 7.6 ± 0.2 | 0.5 ± 0.5 | 0.3 ± 0.1 |
| Pd/C & $Nb_2O_5$ | 47.5 ± 0.7 | 26.6 ± 0.5 | 20.8 ± 0.3 | 4.9 ± 0.1 | 0.2 ± 0.2 | 0 |
| Pd/C & $Nb_2O_5$—$PO_4$ | 25.6 ± 1.0 | 19.1 ± 0.1 | 43.5 ± 0.7 | 10.3 ± 0.5 | 0.5 ± 0.1 | 0.8 ± 0.1 |
| Pd/$Nb_2O_5$—$PO_4$ | 31.5 ± 0.5 | 15.1 ± 0.4 | 42.2 ± 0.4 | 9.0 ± 0.1 | 0.9 ± 0.1 | 0.8 ± 0.1 |
| Pd/C & $NbOPO_4$ | 11.6 ± 1.8 | 18.0 ± 1.2 | 54.8 ± 0.9 | 10.0 ± 0.6 | 0.8 ± 0.2 | 4.8 ± 0.0 |
| Pd/$NbOPO_4$ | 13.8 ± 0.4 | 9.5 ± 0.5 | 62.7 ± 0.6 | 10.3 ± 0.2 | 1.3 ± 0.1 | 2.9 ± 0.2 |

TABLE 8

Material properties of fresh, spent, and regenerated single-phase catalysts.

| Single Phase Catalyst | Surface Area ($m^2\ g^{-1}$) | Pore Vol ($cm^3\ g^{-1}$) | Total Acidity ($\mu mol\ g^{-1}$) | Pd Site Density ($\mu mol\ g^{-1}$) | CO Chemi Pd NP Diameter (nm) | Scherrer Pd NP Diameter (nm) | TEM Pd NP Diameter (nm) |
|---|---|---|---|---|---|---|---|
| Fresh Pd—$Nb_2O_5$—$PO_4$ | 57 | 0.12 | 120 | 16 | 16 | 13 | N/A |
| Fresh Pd—$TiO_2$—$PO_4$ | 134 | 0.38 | 272 | 35 | 8 | 6 | N/A |
| Fresh Pd—$NbOPO_4$ | 131 ± 2 | 0.28 ± 0.01 | 358 ± 48 | 16 ± 3 | 15 ± 1 | 10 ± 2 | 10 ± 9 |
| 117 h Spent Pd—$NbOPO_4$ | 99 | 0.24 | 274 | 2 | 145 | N/A | 9 ± 6 |
| Regen 1x Pd—$NbOPO_4$ | 132 | 0.29 | 384 | 10 | 27 | 11 | N/A |
| Regen 4x Pd—$NbOPO_4$ | 116 | 0.26 | 364 | 8 | 34 | 14 | 5 ± 6 |

Figure 21A:
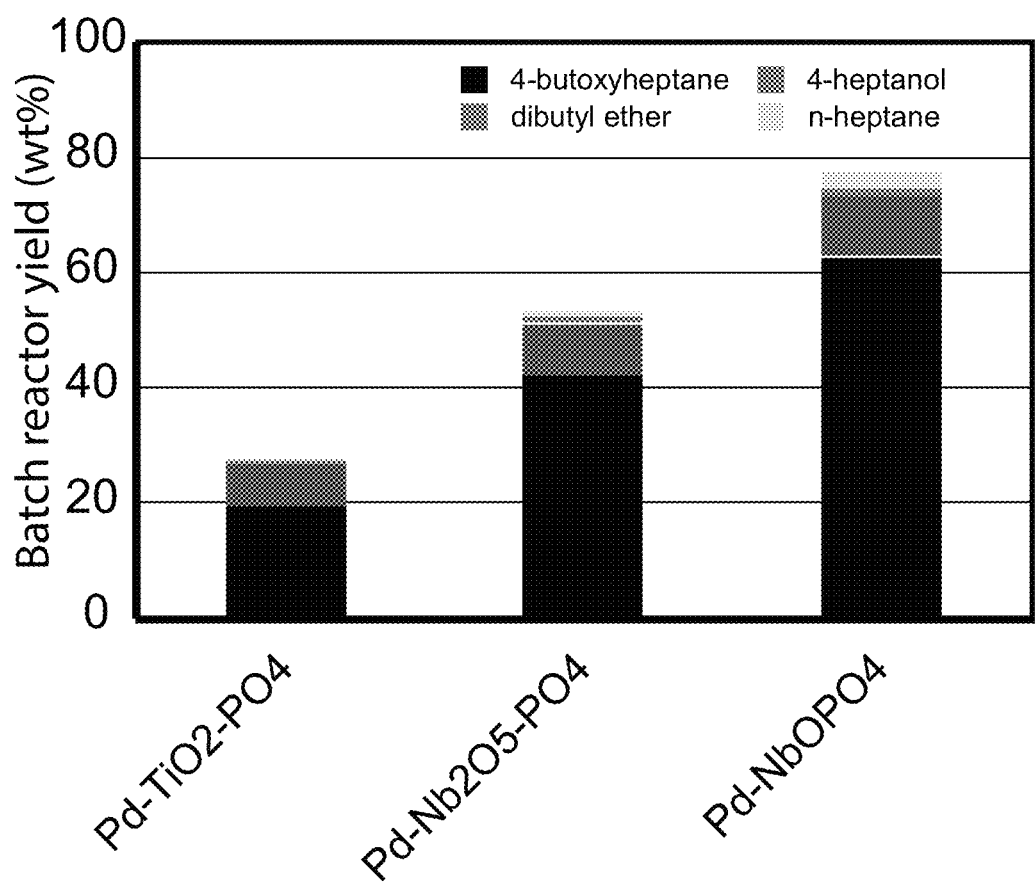
FIG. 21A illustrates single-phase catalyst batch reactor screening results, according to some embodiments of the present disclosure.
Figure 21B:
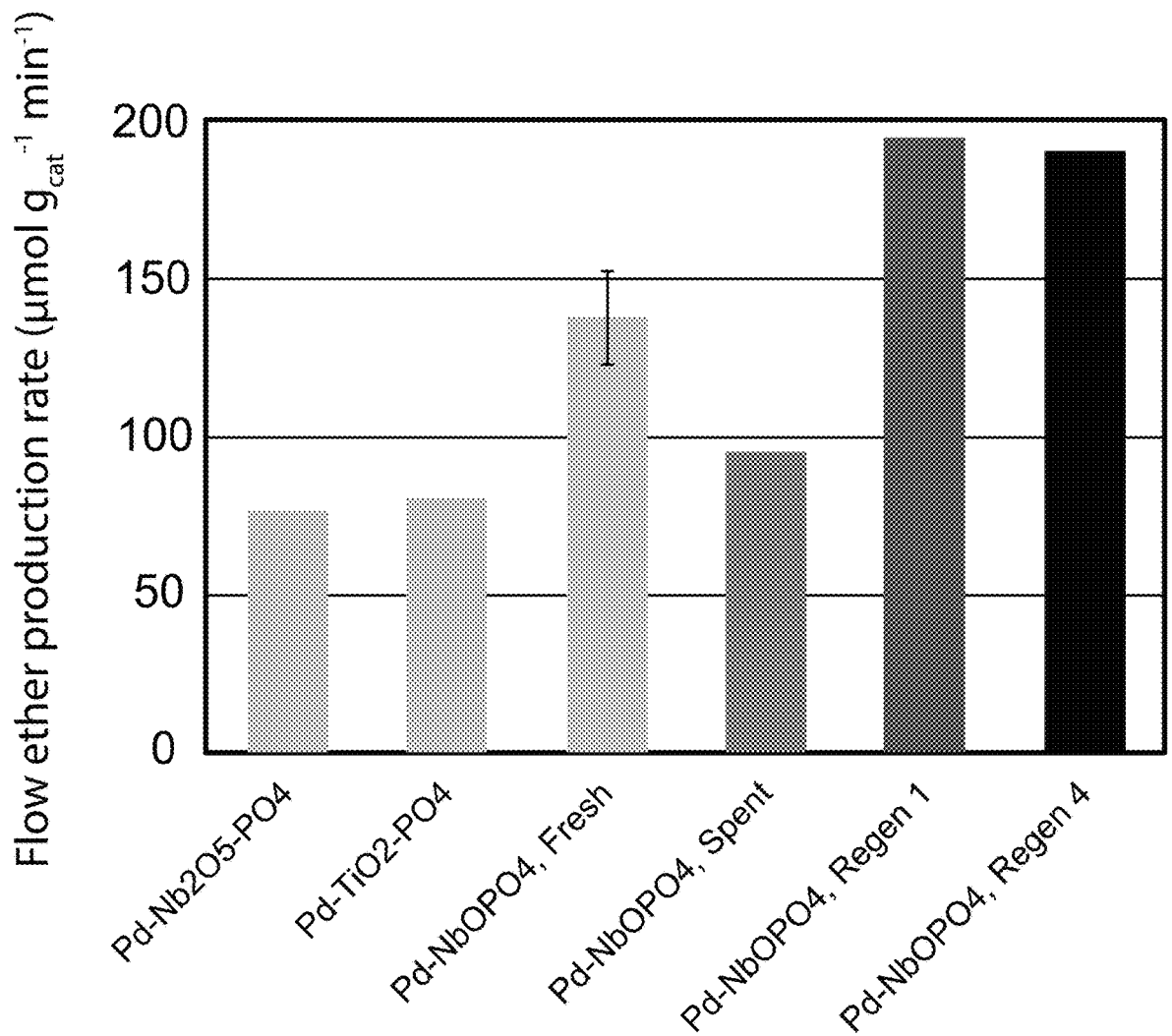
FIG. 21B illustrates flow reactor testing results, according to some embodiments of the present disclosure.

The three single-phase catalysts were then evaluated to compare 4-BH yields and selectivity under batch and flow reactor conditions. In batch (see FIG. 21A), similar selectivity to 4-BH was seen for both Pd/$TiO_2$—$PO_4$ and Pd/$Nb_2O_5$—$PO_4$ relative to the binary physical mixtures of metal oxide and Pd/C, albeit with slightly lower conversion. Pd/$NbOPO_4$ was the highest yielding catalyst for 4-BH, with comparable selectivity. This may be due to the larger Pd metal crystallite sizes or higher total acidity. In flow reactor tests at ~30% molar 4-heptanone conversion (see FIG. 21B), Pd/$NbOPO_4$ also displayed a significantly higher ether production rate of 138±15 $\mu mol\ g_{cat}^{-1}\ min^{-1}$, when compared Pd/$Nb_2O_5$—$PO_4$ and Pd/$TiO_2$—$PO_4$ which ranged from 76 to 81 $\mu mol\ g_{cat}^{-1}\ min^{-1}$, respectively. Interestingly, Pd/$Nb_2O_5$—$PO_4$ showed lower activity than Pd/$TiO_2$—$PO_4$ at low conversion in flow when compared to batch results. Based on these findings, Pd/$NbOPO_4$ was selected for further study.

Figure 22:
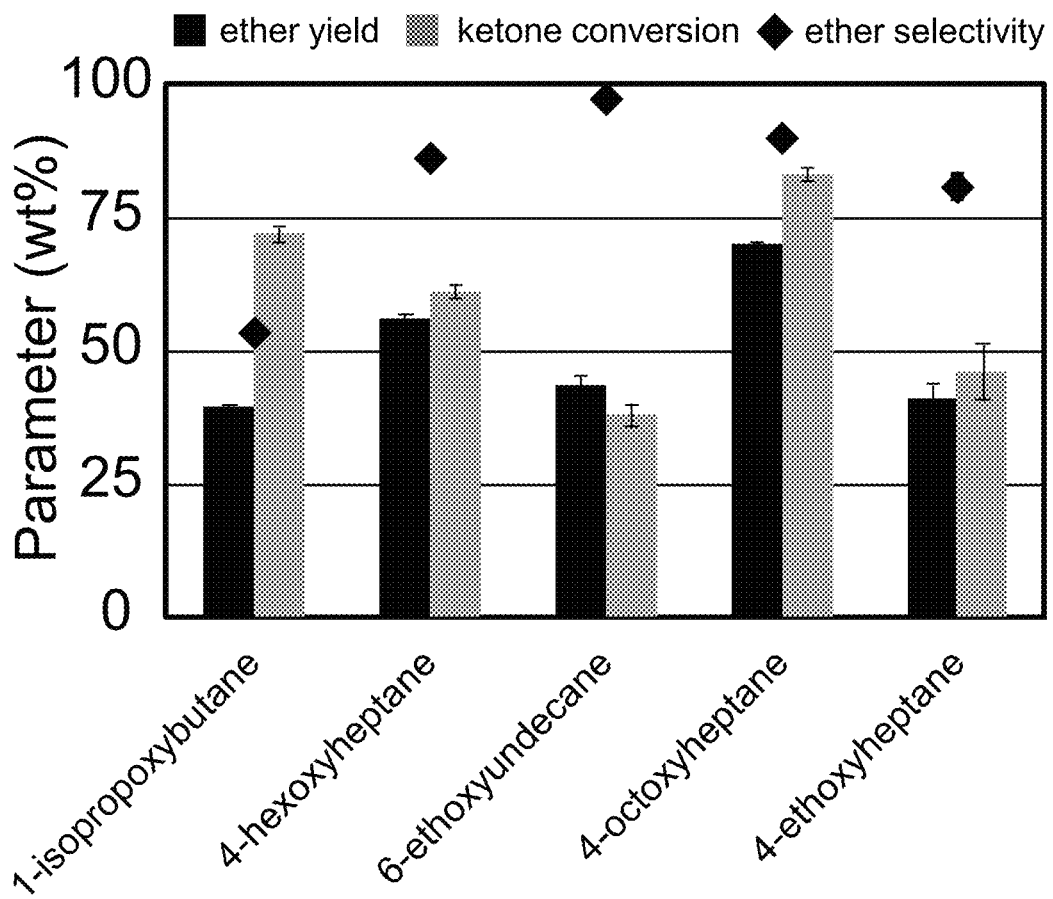
FIG. 22 illustrates the application of Pd/NbOPO$_4$ to produce a variety of branched ether compounds via reductive etherification, with relevant diesel bioblendstock fuel properties provided in Table 7, according to some embodiments of the present disclosure.

The broad applicability of Pd/$NbOPO_4$ to produce ether diesel bioblendstocks was then demonstrated with a range of alcohols (C2-C8) and ketones (C3-C11). Target ether yields ranged from 40-70 wt % and mass selectivity was above 80% for all ethers apart from 1-isopropoxybutane (53%), as shown in FIG. 22. The low selectivity to 1-isopropoxybutane may be due to high reactivity of acetone under these conditions. Fuel properties of the novel ether bioblendstocks were then evaluated using predictive and experimental tools. Fuel property predictions alleviated the need for separation and purification of product reaction mixtures, as well as sample volume requirements required with traditional measurement techniques. Select fuel property measurements are provided in Table 9 for reference.

TABLE 9

Measured and predicted fuel properties (latter in parentheses) for ether bioblendstocks.

| | Cetane Number | Yield Sooting Index | Lower Heating Value (MJ $kg^{-1}$) | Melting Point (° C.) | Flashpoint (° C.) | Boiling Point (° C.) |
|---|---|---|---|---|---|---|
| Conventional base diesel * | 44 | 215 | 43 | −10 | 61 | 333 |
| Target oxygenate blendstock properties | >40 | <200 | >25 | <0 | >52 | <338 |
| 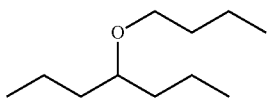 4-butoxyheptane | 80 (76) | 58 (55) | 39 (40) | <−80 (−53) | 64 (60) | 198 (195) |
| 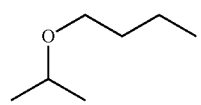 1-isopropoxybutane | (76) | (24) | (38) | (−74) | (1) | (107) |
| 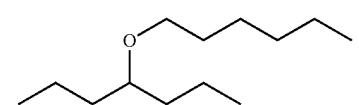 4-hexoxyheptane | (71) | 75 (78) | 43 (41) | <−80 (−4) | 68 (83) | 234 (233) |

TABLE 9-continued

Measured and predicted fuel properties (latter in parentheses) for ether bioblendstocks.

| | Cetane Number | Yield Sooting Index | Lower Heating Value (MJ kg$^{-1}$) | Melting Point (° C.) | Flashpoint (° C.) | Boiling Point (° C.) |
|---|---|---|---|---|---|---|
| 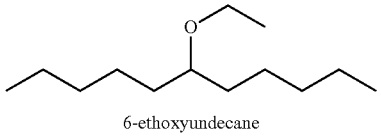 6-ethoxyundecane | (74) | 70 (78) | 42 (41) | 10 (−4) | 83 (82) | 236 (233) |
| 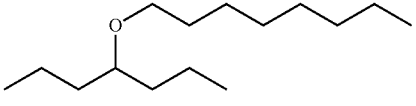 4-octoxyheptane | (81) | (92) | (41) | (18) | (106) | (268) |
| 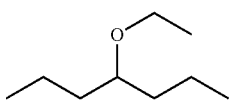 4-ethoxyheptane | (63) | (35) | (39) | −68 (−50) | (31) | (152) |

Certain property criteria, such as melting and boiling point, are useful to ensure consistent phase behaviour in the engine environment in order to facilitate efficient fuel utilization. The melting point of the diesel fuel must be below 0° C. to prevent the fuel from freezing in cold weather, and the boiling point must stay below 338° C. so it can be vaporized. These metrics can be in opposition and require an optimization of blendstock candidate molecular structure and carbon number. The minimum flashpoint criterion of 52° C. ensures safe handling with respect to flammability. Finally, a high LHV indicates an energy dense fuel, which has positive implications for diesel fuel tank mileage.

All ether bioblendstocks displayed predicted cetane numbers ranging from 63-81, which is >40% above the base petroleum diesel value of 44 and advantageous when blending into low cetane fuels. Likewise, yield sooting index values ranged from 24-78, which is >60% below the base diesel value of 215. Lower heating values ranged from 38-43 MJ kg$^{-1}$ due to the aliphatic chains and total carbon numbers that ranged from C7-C15. Although ether energy density values were lower than the base diesel, they all fell within 12%. The branched ether backbone facilitated melting points below freezing when the backbone was below C15. Lastly, C11 and above ethers passed the flashpoint cut-off for flammability, while the C7 and C9 ethers did not, which would limit their blend level in diesel.

Figure 23A:
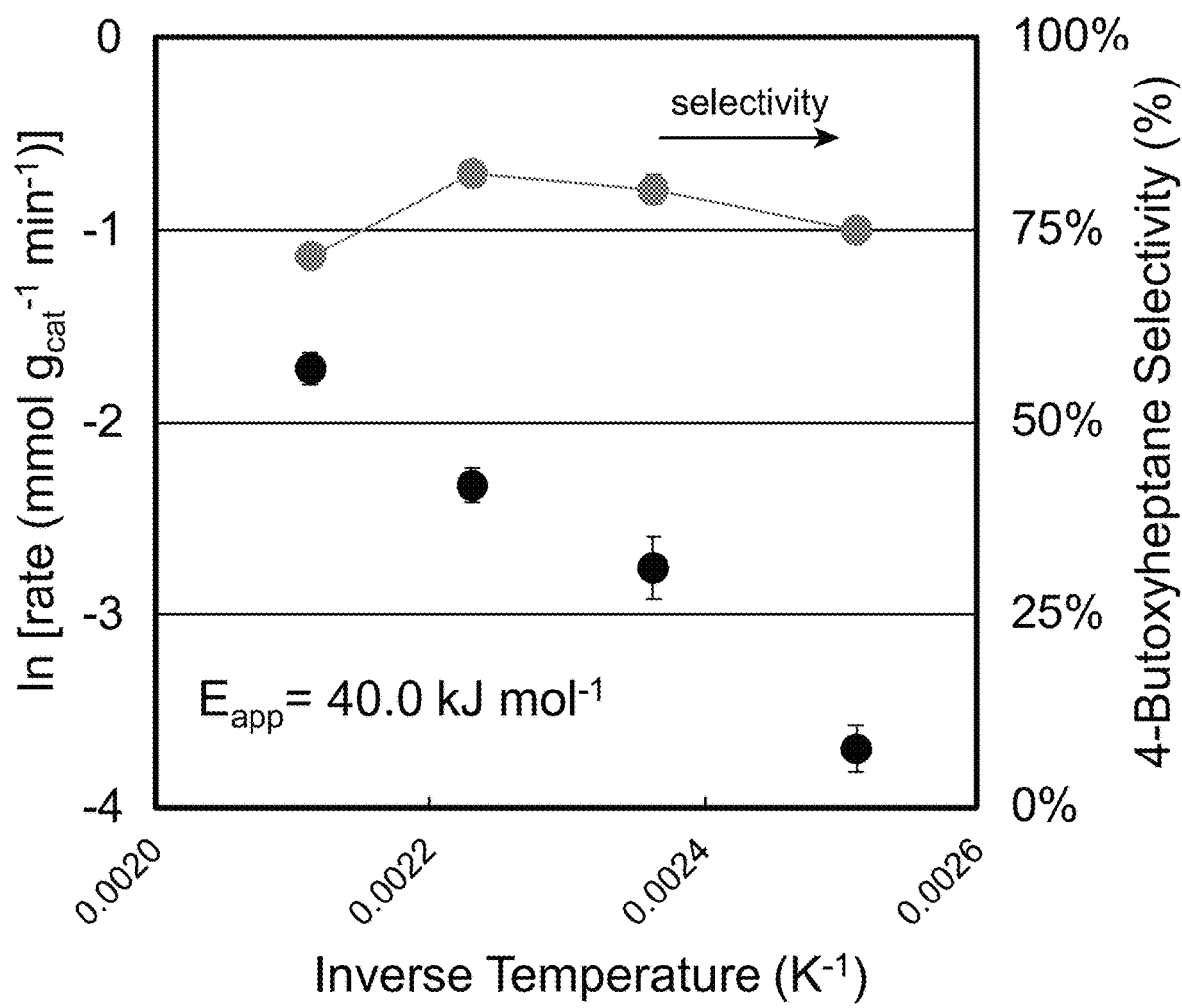
FIG. 23A illustrates the initial rate of 4-BH formation and 4-BH selectivity vs. temperature with the apparent activation energy noted, according to some embodiments of the present disclosure.

Further testing of Pd/NbOPO$_4$ was performed in a trickle bed reactor to assess its temperature dependence for reductive etherification, as well as time-on-stream stability. Tests were performed at 190° C. and 1000 psig H$_2$ with 30 cm$^3$ (STP) min$^{-1}$ of gas flowrate, 0.05 mL min$^{-1}$ of equimolar 4-heptanone and n-butanol feed, and 0.5 g of catalyst. Pd/NbOPO$_4$ production rates and selectivity for 4-BH were measured at four reaction temperatures and 4-heptanone molar conversion below 50% after 17 h time-on-stream, with results shown in FIG. 23A. An apparent activation energy of 40.0 kJ mol$^{-1}$ for the three-step reaction was calculated. The reduced selectivity to 4-BH formation at 200° C. and 125° C. suggests a local maximum is present. While polymeric resins containing sulfuric acid functionalities are commonly used as acid catalysts due to their high Brønsted acidity, their lack of thermal stability (120° C. maximum for Amberlyst-15) prevents operation at the temperatures examined here.

Figure 23B:
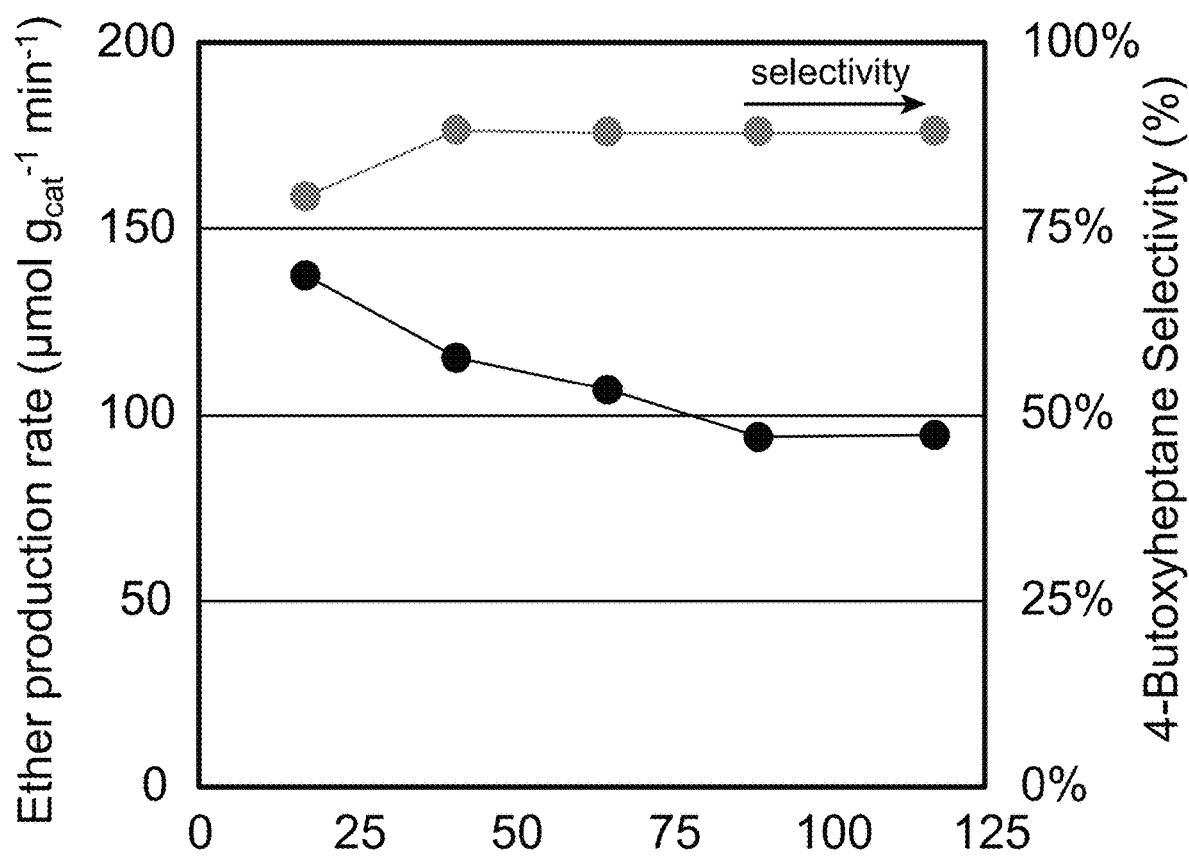
FIG. 23B illustrates time-on-stream evaluation of 4-BH production rate and selectivity, according to some embodiments of the present disclosure.

Pd/NbOPO$_4$ stability was then evaluated under partial conversion conditions (36% molar conversion of 4-heptanone) for over 100 h of time on stream. As shown in FIG. 23B, a steady decline in 4-BH production rate from 138 to 95 μmol g$_{cat}^{-1}$ min$^{-1}$ was seen over the course of the 117-h test. The deactivation was attributed to carbon laydown, which was measured to be 10 wt % of the spent catalyst after reaction by thermal gravimetric analysis-Fourier transform infrared spectroscopy (TGA-FTIR). However, the selectivity to 4-BH increased to 88% after an initial start-up value of 79% due to a sharp drop in 4-heptanol and heptane formation, which may be due to carbon laydown blocking acidic dehydration sites and metallic Pd hydrogenation sites. Corresponding drops in surface area, total acidity and Pd site density were also observed in the spent catalyst (see Table 8).

Reactor effluents at 33 hours were analysed for Pd leaching due to the detrimental effect on catalyst lifetime. Tests showed promising sub-ppm levels of Pd leaching levels, with 19 ppb for Pd/NbOPO$_4$, 8 ppb for Pd/Nb$_2$O$_5$—PO$_4$, and below detection limit of ~6 ppb for Pd/TiO$_2$—PO$_4$. Phosphorus leaching for Pd/NbOPO$_4$ was also tested using ASTM D3231 due to concerns of corrosion with engine metal components. Results showed 0.38 ppm P in the effluent, which is far below the 10 ppm limit of B100 biodiesel. TEM imaging of the spent catalysts showed little change in Pd NP sizes after 117 h of time on stream, with a decrease in average Pd particle size from 10±9 nm to 9±6 nm for the 117-h sample, as seen in Panels D and E of FIG. 20A and Panel B of FIG. 20B.

Catalyst regeneration was evaluated by cycling reduction and oxidation at elevated temperatures to determine the impact on material properties and reductive etherification performance. As-synthesized Pd/NbOPO$_4$ was treated with either 1 or 4 cycles of oxidation under zero air at 350° C. and reduction under H$_2$ at 265° C. At this temperature, 92% of the carbon had been removed from the spent catalyst during TGA-FTIR. As shown in Table 6, negligible changes in surface area and total acidity of the NbOPO$_4$ support occurred after regeneration. However, Pd surface area from CO chemisorption measurements decreased substantially after regeneration, suggesting Pd sintering. While the Scherrer crystallite size measurement from XRD spectra showed small increases in Pd nanoparticle size, TEM imaging revealed a more complex distribution. The regenerated samples showed a sharp increase in the number of small Pd crystals (<4 nm), with an average size of 5±6 nm (see Panels G and H of FIG. 20A and Panel C of FIG. 20B). The number of larger Pd NPs remained fairly constant however which accounts for the small changes in XRD and CO chemisorption results. Interestingly, the regenerated catalyst displayed the highest ether production rates of 195 μmol $g_{cat}^{-1}$ min$^{-1}$ despite the drop in Pd dispersion, which remained stable after 4-regeneration cycles (190 μmol $g_{cat}^{-1}$ min$^{-1}$), as shown in see FIG. 21B.

Methods:

Batch reactor. Reductive etherification experiments were performed in a Parr multi-batch reactor system for preliminary screening of reaction conditions (Parr Instrument Co.). Feed solution and catalyst (5 wt % Palladium on activated carbon from Sigma Aldrich and Amberlyst-15 resin) were added to 75-mL reactor cups, followed by purging and flushing of the system with He for three cycles. The reactors were then purged and flushed with hydrogen three times and pressurized to the desired level before being sealed and heated to the desired temperature over a period of ~20 min. Reaction solution and catalyst were well mixed by using magnetic stir bars operating at 800 rpm. Reactors were quenched in an ice bath to terminate the reaction at predetermined time. Products were filtered through 0.2-μm PTFE membranes to separate the liquid from the catalysts and analyzed by GC/MS and GC/Polyarc-FID.

Continuous Flow Reactor. Continuous flow reactor testing was performed using a custom reactor system operated in a down-flow trickle bed configuration. The reactor system was outfitted with an HPLC pump (Scientific Instrument Series I) to deliver liquid phase reactants, mass flow controllers (Brooks Instrument) for gas delivery control, tube-in-tube heat exchanger for cooling the reactor effluent, high-pressure 100 ml or 600 mL stainless steel knockout pot (Parr) with bottom sampling valve, and an electronically controlled backpressure regulator (Brooks) to maintain system pressure. Reactions were performed with gas and liquid reagents fed to through the top of a 15-17" long, ½" or ¾" outer-diameter stainless steel reaction tube with Dursan surface inert coating. A clamshell furnace was used to maintain uniform heating across the catalyst bed. The reaction mixture included commercial 1-butanol and 4-heptanone (Sigma Aldrich) mixed in 1:1 molar ratio which was delivered at a flow rate to achieve a WHSV of 1.0-1.1 The catalyst bed included Amberlyst-15 ion exchange resin (Sigma-Aldrich) ground to less than 100 mesh (<150 um) mixed with 5 wt % palladium on carbon powder (Sigma-Aldrich, used as supplied) in a 3:1 weight ratio. The catalyst bed was positioned in the center of the thermal stability zone of the clamshell furnace. Reactor tube packing was performed by adding glass wool (Ohio valley, untreated), glass beads (BioSpec Products) and 1 cm of inert quartz sand (Quartz Scientific Inc.) to establish bed position. After adding the catalyst mixture, reactor tube filling was completed with additional sand, glass beads and wool. Sand was used on both sides of the catalyst bed to ensure catalyst retention during reactions. After packing, the reactor tube was installed in the reactor system and the catalyst bed was pre-wetted with the reaction mixture at room temperature and pressure with hydrogen flow for a minimum of 1 hour. After pre-wetting, continuous liquid phase reductive etherification reactions were performed with H$_2$ supplied at a 300-400% molar excess, and system pressure of 1000 psig. Reaction temperature was maintained at 120° C. Liquid effluent samples were collected from the knockout pot periodically and analyzed by GC/MS and GC/Polyarc-FID.

Separations. After reductive etherification of 4-heptanone and 1-butanol was completed in a flow reactor, the target molecule, 4-butoxyheptane, was purified by removing reactants and byproducts. The known components of the solution and their boiling points are summarized in Table 10 below. Some components could not be identified but have distinct boiling points from the target molecule. Water was first removed by pipetting the aqueous layer from the organic layer. 1-butanol was then removed via rotary evaporation under reduced pressure due to its high volume—percent and its significantly lower boiling point relative to the target. The remaining higher-boiling point compounds were transferred to a 250 mL round-bottom flask containing about 1 g of boiling chips, fitted with a custom thermowell for separation in a BR Instruments Spinning Band Distillation unit. A slowly increasing temperature ramp was applied under reduced pressure to boil off each compound, and subsequent fractions were collected for GC analysis, confirming a high purity 4-butoxyheptane fraction (93-98% pure) with a balance of 4-hydroxy-4-methyl-2-pentanone and unknowns in very small quantities. It should be noted that the fractions containing high-purity 1-butanol and 4-heptanone could be reused as reactants for future reactions.

TABLE 10

GC-MS profile of 4-butoxyheptane after 6 weeks of aging

| Name | $T_{boil}$ (° C.) |
|---|---|
| 4-butoxyheptane | 198 |
| 4-heptanol | 161 |
| 4-heptanone | 144 |
| n-butyl ether | 141 |
| n-butanol | 118 |
| Water | 100 |
| Heptane | 98 |

Gas chromatography (GC). Samples obtained from reductive etherification were analyzed via an Agilent 7890 GC system with Polyarc-FID-MS detection for confirmation of compound identity and estimation of compound concentration and purity. The Polyarc (Activated Research Company) is a catalytic system which converts organic compounds to methane. The resulting methane is then analyzed with traditional FID. This allows quantitation of chromatographically separated compounds by comparison of FID area response for most compounds irrespective of compound class. Calculation of compound concentration in the sample with the Polyarc-FID system is based on the equation: Carbon(sample) Area(sample)*Carbon(standard)/Area (standard). The GC system incorporated a split plate which allowed simultaneous analysis of a separate portion of the GC column eluent by MS detection (i.e., not processed through the Polyarc). GC analysis utilized an HP-5MS column (30 m×0.25 mm), split injection (25:1), injection volume of 1 uL, inlet temperature of 260° C., oven temperature programming (40° C. for 2 min, then 18° C./min to 280° C. for 0 minutes), and helium carrier gas (constant flow mode, 29 cm/sec). Samples were typically prepared by adding 4 uL of sample to 1.0 ml of solvent (usually acetone) plus 4 uL of an alkane (usually nonane) as the internal standard.

Cetane Number. CN (ICN) was measured in an AFIDA (ASTM D8183).

Heating Values. HHV was found using a bomb calorimeter to combust 15 mL of sample (D240), with LHV calculated using sample hydrogen content (D240, Section 10.5.1) measured using a LECO TruSpec CHN determinator. To find hydrogen content, samples were combusted in excess oxygen at 950° C. The amount of $CO_2$ and $H_2O$ produced could then be quantified using IR and using an EDTA calibration standard the hydrogen wt % could be extracted.

Density. A Mettler-Toledo DM40 density meter was used to determine density using D4052.

Viscosity. Viscosity at 40° C. was measured using a shear rate of 1-100 $s^{-1}$ by a TA Instrument AR1500 equipped with a recessed rotor (D975, D445).

Melting point. Melting point and cloud point (for mixtures) were measured using a Phase Technology Series 70× (modified D5773).

Boiling Point. $T_{boil}$ of pure was estimated using T90 of a simulated distillation (D2887), with blend $T_{boil}$ determined using thermogravimetric analysis (TGA).

Flash point. D7094 was used to measure $T_{flash}$ with an average error of ±1.3° C.

Lubricity. Lubricity measured using D6079.

Conductivity. Conductivity measured using D2624.

Acid number. TAN was measured to confirm low corrosivity (D664 Method B).

Yield Sooting Index. YSI was measured using procedures described in work by McEnally et al.[73] The target sample, toluene, and n-heptane were independently doped into the fuel of a methane/air flame at 1000 ppm. The maximum soot concentrations in the resulting flames were determined from their line-of-sight spectral radiance (LSSR) at 660 nm. The LSSR signals for the target samples were linearly re-scaled into a YSI based on the endpoints YSI-heptane=36 and YSI-toluene=170.9

Water Solubility. To determine water solubility, water was saturated with each ether by adding DI water to the samples at a ratio of 1:5 by volume and shaking thoroughly for >1 minute. The mixed samples were left overnight to separate and the amount of ether in the aqueous layer was determined by GC/MS. The purified C11 ether had a water solubility of 15 mg/L. A 20% blend of the ether in diesel resulted in 4 mg/L of the ether extracted to the water layer, with minimal 4-heptanol, 4-heptanone, and 1-butanol also found in the aqueous layer.

Storage stability testing. Aging conditions to test storage stability of the target ether are based on the procedure of ASTM D4625 Standard Test Method for Middle Distillate Fuel Storage Stability. This method accelerates the oxidation rate of diesel fuel by approximately 4-fold, with one week under these conditions equivalent to approximately one month of storage at 21° C. It should be noted that this degree of acceleration has not been validated for ethers, but nonetheless provides a standard protocol for diesel range sample aging. Aging was conducted for 6 weeks (simulating 6 months) with measurement of peroxide concentration at 2-week intervals. Peroxide concentration was measured following AOCS method Cd 8b-90, modified for potentiometric end point detection and smaller sample size. A sample of isoamyl ether (>99%, non-stabilized, Sigma-Aldrich) was aged alongside the 4-butoxyheptane for comparison. Samples of 4-butoxyheptane before and after aging were analyzed by gas chromatography with mass spectrometry (GC-MS) in an attempt to identify components produced by oxidation (see Table 11 below). The ether samples were diluted volumetrically in acetone 1:10. Analysis was conducted with an Agilent 7890A GC coupled with an Agilent 5975C mass selective detector (MSD). The column used for compound separation was a Restek Rtx-50, (50% phenylmethylsiloxane phase) of dimensions 30 m×0.25 mm, 0.25 μm df. The GC settings were as follows: oven initial temperature 50° C., ramp of 7° C./min to 140° C., followed by ramp of 12° C./min to 300° C., hold or 5 minutes. Inlet temperature 275° C., injection volume 1 helium carrier gas flow of 1 mL/min, split ratio 100:1. Transfer line temperature 310° C. The MSD was operated in continuous scan mode from m/z 29 to 600, source temperature 230° C., quad temperature 150° C., and solvent delay set to 1.40 minutes.

TABLE 11

GC-MS profile of 4-butoxyheptane after 6 weeks of aging

| Name | Retention Time | Match Quality | % Total Area |
|---|---|---|---|
| Butanal | 1.69 | 93 | 0.50 |
| Butanoic acid | 2.78 | 95 | 0.40 |
| 4-Heptanol | 3.98 | 93 | 0.10 |
| 4-Heptanone | 4.07 | 95 | 1.90 |
| Formic acid, 2,4-dime thylpent-3-yl ester | 5.10 | 91 | 0.30 |
| Butanoic acid, butyl ester | 6.02 | 95 | 0.20 |
| 4-Butoxyheptane | 6.57 | Manual | 94.90 |
| Unknown | 6.69 | | 0.30 |
| Unknown | 9.33 | | 0.30 |
| 1-[(heptan-4-yl)oxy]butane-1-peroxol | 13.03 | Manual | 0.80 |
| 4-butoxyheptane-4-peroxol | 13.22 | Manual | 0.30 |

Predictive Tools. Two models were used to estimate melting point. The first was sourced from commercial software, ChemDraw Professional 15.1 (PerkinElmer) which exploits both Joback's fragmentation method as well as Stein's modification to Joback's method. The second prediction was obtained from the estimation program MPBP-WIN™ in EPI Suite™ (US EPA, Syracuse Research Corp.). This program estimates melting point by giving a weighted average of the results of two methods, the Joback Method (a group contribution method) and the Gold and Ogle method (a correlation between melting point and boiling point). Boiling point predictions also utilized the ChemDraw and EPI Suite tools, with the addition of a third available predictive model developed by Satou et al. Flashpoint was estimated via two predictive models, both requiring a reliable boiling point. One of the earliest was developed by Butler et al., which was built on correlation for petroleum boiling in the range of about 90 to 370° C. The second correlation was later developed by Prugh and based on a larger database of hydrocarbons and fuel mixtures. Numerous predictive models for the higher heating value for a variety of samples have been developed, primarily based around species mass contributions. The first model applied in this work is the Dulong equation, which was used to determine higher heating value estimates for coal and fossil fuels. This work also includes two predictive estimates which are from modifications to Dulong's formula. Lloyd and Davenport included ethers and other oxygenates in their modification, and Boie adapted the formula for a larger dataset. Lower heating values reported here are determined by the following equation, which is a function of the estimated mass % hydrogen (H) in a sample (ASTM D240, Section 10.5.1).

$$LHV=HHV-(0.2122*H)$$

Cetane number predictions were produced using a back-propagating artificial neural network (ANN) with inputs including experimental CN values and quantitative structure-property relationships (QSPR) for individual molecules. The model uses an iterative regression analysis technique to reduce the number of input parameters; in the case of CN, from >1500 to 15. The ANN randomly assigns an individual molecule from the known data set to one of three conditions: learning, validation, and testing, with proportions of 65%, 25%, and 10% respectively. The trained model was subsequently applied to the new molecule of interest's QSPR parameters in order to produce a predicted CN. The method has been shown to provide high accuracy and repeatability across a broad range of hydrocarbons when predicting CN. Yield sooting index predictions were generated using a group contribution model that sums contributions from each carbon atom.

Catalyst Synthesis. Solid acid catalysts were synthesized by stirring 20 g of metal oxide precursor (niobic acid (CBMM), zirconia (Sigma Aldrich), titania ($TiO_2$, Johnson Matthey) or alumina ($Al_2O_3$, Johnson Matthey)) in 1 M phosphoric acid solution for 48 h. The solid sample was then separated from solution by centrifugation at 8000 rpm for 10 min and washing with deionized water three times. Then, the catalyst powders were dried at 120° C. for 12 h (10° C. $min^{-1}$ ramp) before calcination at 500° C. for 5 h (5° C. $min^{-1}$ ramp). For comparison, metal oxide samples without the phosphating procedure were also dried at 120° C. for 12 h and then calcined at 500° C. for 5 h (5° C. $min^{-1}$ ramp). Single-phase catalysts were then synthesized through a typical incipient wetness procedure. Briefly, 315 mg of Palladium Nitrate Dihydrate (2.5 wt % Pd relative to support) was dissolved in 4 mL of water and mixed with 5 g of phosphated metal oxide under sonication. Then, the catalyst slurries were dried under air at 100° C. for 12 h (10° C. $min^{-1}$ ramp) and 265° C. for 2 h (5° C. $min^{-1}$ ramp).

Ammonia Temperature Programmed Desorption. The total acidity of the solid acid materials was measured by $NH_3$ chemisorption using an Altamira Instruments AMI-390 system. A quartz U-tube was loaded with approximately 100 mg of sample and pretreated at 500° C. for 1 h under flowing helium (5° C. $min^{-1}$ ramp). Ammonia was dosed to the samples with a mixture of 10% (v/v) $NH_3$/He flowed for 1 h at 120° C. and the sample line was flushed with He flow for 1 h at 120° C. Then, ammonia was desorbed by cooling to 30° C. before ramping to 500° C. at 30° C. $min^{-1}$ and holding for 30 min. Pyridine DRIFTS. Relative densities of Brønsted and Lewis acid sites on the solid acid materials were determined using pyridine adsorption diffuse reflectance Fourier transform infrared spectroscopy (Pyr-DRIFTS). Measurements were taken using a Thermo Nicolet iS50 FT-IR spectrometer equipped with a Harrick Praying Mantis reaction chamber. Solid acid samples were pretreated at 350° C. for 2 h (5° C. $min^{-1}$ ramp) under flowing Ar. Samples were then cooled to 150° C. and purged with Ar for 10 min before collecting a background spectrum. Next, the samples were dosed with pyridine vapor for 5 min by flowing argon (Ar) through a pyridine-filled bubbler at room temperature and physisorbed pyridine was subsequently desorbed under Ar by heating to 200° C. (5° C. $min^{-1}$ ramp) and holding for 30 min. After cooling to 150° C., 64 scans were collected at 4 $cm^{-1}$ resolution, averaged and the background was subtracted. The relative ratio of Brønsted to Lewis acidic sites was then determined using the peak area of vibrational modes near 1445 $cm^{-1}$ (Lewis) and 1540 $cm^{-1}$ (Brønsted).

Thermogravimetric Analysis. To analyze the hygroscopic nature of the materials, the solid acid samples were kept in a sealed container with a saturated $H_2O$ atmosphere for 72 h and then directly examined by thermogravimetric analysis (TGA). These measurements were performed using a Q-Series 500 Thermogravimetric Analyzer (TA Instruments) with aluminum pans and the Hi-Res Dynamic heating function from room temperature to 150° C. with a baseline ramp rate of 10 K/min.

Water Absorption Isotherms. The water absorption capacity for solid acid materials was measured from $H_2O$ isotherms collected at 18° C. using a Quantachrome Autosorb 1-C. The samples were degassed under vacuum at 200° C. (except for Amberlyst-15 which was degassed at 100° C.) for 20 h immediately before performing the measurement.

Whether or not a reactant or product described herein is "bioderived" may be determined by analytical methods. Using radiocarbon and isotope ratio mass spectrometry analysis, the bio-based content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pNMC value obtained correlates directly to the amount of biomass material present in the sample. Thus, ASTM-D866 may be used to validate that the compositions described herein are and/or are not derived from renewable sources.

TABLE 12

Fuel properties and composition of the surrogate diesel

| Composition | Molar % | Wt % | Vol % |
| --- | --- | --- | --- |
| a-Methylnaphthalene | 12.39 | 9.92 | 8.12 |
| trans-Decalin | 20.08 | 15.61 | 14.99 |
| 2,2,4,4,6,8,8-Heptamethylnonane | 19 | 24.2 | 26.11 |
| n-Butylcyclohexane | 10.5 | 8.28 | 8.67 |
| n-Hexadecane | 16.61 | 21.15 | 22.89 |
| Tetralin | 13.78 | 10.25 | 8.83 |
| n-Dodecylebenzene | 7.64 | 10.59 | 10.39 |
| Total | 100 | 100 | 100 |
| Properties | | | |
| Cetane Number (ICN D8183) | | 44.5 | |
| Density (g/mL) | | 0.843 | |
| Cloud point (° C.) | | −10.5 | |

Example Set #1

Example 1. A composition comprising: a first oxide comprising a phosphate; a ratio of Brønsted acid sites to Lewis acid sites between 0.05 and 1.00; and a total acidity between 50 μmol/g and 300 μmol/g, wherein: the phosphate is at least one of a functional group covalently bonded to the first oxide or an anion ionically bonded to the first oxide.

Example 2. The composition of Example 1, wherein the first oxide comprises a metal comprising at least one of a first transition metal, aluminum, silicon, lanthanum, or magnesium.

Example 3. The composition of Example 2, wherein the first transition metal comprises at least one of niobium, zirconium, aluminum, titanium, tantalum, hafnium, scandium, yttrium, tungsten, or molybdenum.

Example 4. The composition of Example 3, wherein the first oxide comprises at least one of $Nb_2O_5$, $ZrO_2$, $Al_2O_3$, $TiO_2$, $WO_3$, or $MoO_3$.

Example 5. The composition of Example 4, wherein the phosphated first oxide comprises at least one of $Nb_2O_5$—$PO_4$, $TiO_2$—$PO_4$, $ZrO_2$—$PO_4$, $NbOPO_4$, $ZrO_2$—$PO_4$, $WO_3$—$PO_4$, $Ti(HPO_4)_2$, or $Zr(HPO_4)_2$.

Example 6. The composition of Example 1, further comprising a surface area between about 40 m²/g and about 500 m²/g.

Example 7. The composition of Example 1, further comprising a pore volume between 0.05 cm³/g and about 1.0 cm³/g.

Example 8. The composition of Example 1, further comprising: a particle positioned on a surface of the first oxide, wherein: the particle comprises a second transition metal.

Example 9. The composition of Example 8, wherein the second transition metal comprises at least one of palladium, platinum, ruthenium, rhodium, iridium, molybdenum, nickel, cobalt, or copper.

Example 10. The composition of Example 8, wherein the particle has a characteristic length between about 0.1 nm and about 10 μm.

Example 11. The composition of Example 10, wherein the characteristic length is between about 0.1 nm and about 50 nm.

Example 12. The composition of Example 8, wherein the particle has a characteristic length between about 10 μm and about 3 mm.

Example 13. The composition of Example 8, wherein a concentration of the particle is between about 0.1 wt % and about 15 wt %.

Example 14. The composition of Example 13, wherein the concentration is between about 1 wt % and about 15 wt %.

Example 15. The composition of Example 1, further comprising: a second oxide that is different than the first oxide, wherein: the second oxide forms a core having a surface, and the first oxide forms a shell covering substantially all of the surface.

Example 16. The composition of Example 15, wherein the shell has a thickness between about 1 nm and 10 μm.

Example 17. The composition of Example 15, wherein the shell has a thickness between about 1 nm and 100 nm.

Example 18. The composition of Example 15, wherein the second oxide comprises at least one of $Nb_2O_5$, $ZrO_2$, $Al_2O_3$, or $TiO_2$.

Example Set #2

Example 1. A composition comprising: a first mixture comprising an ether defined by

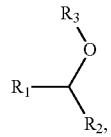

wherein: each of $R_1$ and $R_2$ comprise a hydrogen atom or an aliphatic group, and $R_3$ comprises an aliphatic group.

Example 2. The composition of Example 1, wherein $R_1$ and $R_2$ are different.

Example 3. The composition of Example 1, wherein $R_1$ and $R_3$ are different.

Example 4. The composition of Example 1, wherein $R_2$ and $R_3$ are different.

Example 5. The composition of Example 1, wherein each of $R_1$, $R_2$, and $R_3$ are different.

Example 6. The composition of Example 1, wherein each of $R_1$, $R_2$, and $R_3$ are the same.

Example 7. The composition of Example 1, wherein each of $R_1$, $R_2$, and $R_3$ comprises between 1 and 30 carbon atoms, inclusively.

Example 8. The composition of Example 7, wherein each aliphatic group comprises at least one of an alkyl group, an alkenyl group, or an alkynyl group.

Example 9. The composition of Example 8, wherein the ether comprises at least one of 4-butoxyheptane, 1-isopropoxybutane, 4-hexoxyheptane, 6-ethoxyundecane, 4-octoxyheptane, 4-ethoxyheptane, dibutyl ether, or ethyl tetrahydrofurfuryl ether.

Example 10. The composition of Example 1, wherein the first mixture further comprises at least one of an alcohol or a ketone.

Example 11. The composition of Example 10, wherein the alcohol comprises at least one of a linear alcohol or a branched alcohol having between 2 and 20 carbon atoms, inclusively.

Example 12. The composition of Example 11, wherein the alcohol comprises at least one of ethanol, propanol, butanol, or pentanol.

Example 13. The composition of Example 10, wherein the alcohol comprises at least one of a cyclic alcohol, a diol, or furfuryl alcohol.

Example 14. The composition of Example 10, wherein the ketone comprises at least one of a diketone, a cyclic ketone, a linear ketone, or a branched ketone having between 3 and 20 carbon atoms, inclusively.

Example 15. The composition of Example 14, wherein the ketone comprises at least one of a butanone, a pentanone, a hexanone, a heptanone, or an octanone.

Example 16. The composition of Example 10, wherein the ether is present in the first mixture at a concentration between about 1 wt % and about 100 wt %.

Example 17. The composition of Example 16, wherein the concentration of the ether is between about 20 wt % and about 80 wt %.

Example 18. The composition of Example 1, further comprising a second mixture comprising at least one of a diesel fuel or a gasoline fuel.

Example 19. The composition of Example 18, wherein the first mixture is present at a concentration between about 10 vol % and about 100 vol %.

Example 20. The composition of Example 19, wherein the concentration is between about 10 vol % and about 30 vol %.

Example 21. The composition of Example 1, further comprising a CN value greater than 40.

Example 22. The composition of Example 1, further comprising an LHV value greater than 25 MJ/kg.

Example 23. The composition of Example 1, further comprising an LHV value greater than 36 MJ/kg.

Example 24. The composition of Example 1, further comprising a water solubility less than 2 g/L.

Example Set #3

Example 1. A method comprising reacting in the presence of a solid catalyst, diatomic hydrogen gas with a mixture comprising an alcohol and a ketone, wherein the reacting results in the forming of an ether.

Example 2. The method of Example 1, wherein: the solid catalyst comprises: a first oxide comprising a phosphate; a ratio of Brønsted acid sites to Lewis acid sites between 0.05 and 1.00; and a total acidity between 50 µmol/g and 300 µmol/g, wherein: the phosphate is at least one of functional group covalently bonded to the first oxide or an anion ionically bonded to the first oxide.

Example 3. The method of Example 1, wherein the alcohol comprises at least one of a linear alcohol or a branched alcohol having between 2 and 20 carbon atoms, inclusively.

Example 4. The method of Example 1, wherein the ketone comprises at least one of a diketone, a cyclic ketone, a linear ketone, or a branched ketone having between 3 and 20 carbon atoms, inclusively.

Example 5. The method of Example 1, wherein the reacting is performed at a temperature between about 50° C. and about 300° C.

Example 6. The method of Example 5, wherein the reacting is performed at a temperature between about 100° C. and about 200° C.

Example 7. The method of Example 1, wherein the reacting is performed at a pressure between about 0 psig and about 2000 psig.

Example 8. The method of Example 7, wherein the reacting is performed at a pressure between about 0 psig and about 1000 psig.

Example 9. The method of Example 1, wherein the reacting is performed with the hydrogen gas at a partial pressure between about 0 psig and about 2000 psig.

Example 10. The method of Example 9, wherein the reacting is performed with the hydrogen gas at a partial pressure between about 0 psig and about 1000 psig.

Example 11. The method of Example 1, wherein the reacting is performed in a batch reactor.

Example 12. The method of Example 11, wherein the reacting is performed for a period of time between about 1 hour and about 10 hours.

Example 13. The method of Example 12, wherein the period of time is between about 1 hour and about 5 hours.

Example 14. The method of Example 1, wherein the reacting is performed in a flow reactor.

Example 15. The method of Example 14, wherein the reacting is performed at a WHSV between about 0.1 h$^{-1}$ and about 10 h$^{-1}$.

Example 16. The method of Example 15, wherein the WHSV is between about 1 h$^{-1}$ and about 2 h$^{-1}$.

Example 17. The method of Example 1, wherein the mixture further comprises a non-reactive solvent.

Example 18. The method of Example 17, wherein the non-reactive solvent comprises at least one of a hexane or a chlorinated molecule.

Example 19. The method of Example 17, wherein the chlorinated molecule comprises at least one of chloroform or dichloromethane.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
a first mixture comprising 4-butoxyheptane; and
a cetane number (CN) value greater than 39.

2. The composition of claim 1, wherein the first mixture further comprises at least one of 4-heptanone, 4-heptanol, n-butanol, heptane, or n-butyl ether.

3. The composition of claim 1, wherein the first mixture further comprises at least one of 1-isopropoxybutane, 4-hexoxyheptane, 6-ethoxyundecane, 4-octoxyheptane, 4-ethoxyheptane, dibutyl ether, or ethyl tetrahydrofurfuryl ether.

4. The composition of claim 3, wherein the first mixture further comprises at least one of ethanol, furfuryl alcohol, or butanone.

5. The composition of claim 1, further comprising a second mixture comprising at least one of a diesel fuel or a gasoline fuel.

6. The composition of claim 5, wherein the first mixture is present at a concentration between about 10 vol % and about 100 vol %.

7. The composition of claim 1, further comprising an LHV value greater than 25 MJ/kg.

8. The composition of claim 1, further comprising an LHV value greater than 36 MJ/kg.

9. The composition of claim 1, further comprising a water solubility less than 2 g/L.

10. The composition of claim 1, wherein the first mixture is bioderived.

11. The composition of claim 1, wherein the composition is a liquid.

12. The composition of claim 11, wherein the composition performs suitably as a diesel fuel or a gasoline.

\* \* \* \* \*